US006852110B2

United States Patent
Roy et al.

(10) Patent No.: US 6,852,110 B2
(45) Date of Patent: Feb. 8, 2005

(54) NEEDLE DEPLOYMENT FOR TEMPERATURE SENSING FROM AN ELECTRODE

(75) Inventors: Loren L. Roy, Scotts Valley, CA (US); Timothy G. Dietz, Califon, NJ (US); Stanley Levy, Jr., Saratoga, CA (US); F. Allen House, Pleasanton, CA (US); Carine Hoarau, Pleasant Hill, CA (US); Peter A. Tobisch, Santa Cruz, CA (US)

(73) Assignee: Solarant Medical, Inc., Livermore, CA (US)

( * ) Notice: Subject to any disclaimer, the term of this patent is extended or adjusted under 35 U.S.C. 154(b) by 61 days.

(21) Appl. No.: 10/211,973

(22) Filed: Aug. 1, 2002

(65) Prior Publication Data

US 2004/0024433 A1 Feb. 5, 2004

(51) Int. Cl.$^7$ .............................................. A61B 18/18
(52) U.S. Cl. ........................................ 606/41; 607/101
(58) Field of Search .............................. 607/96, 98, 99, 607/101, 102; 606/41–45, 49, 50

(56) References Cited

U.S. PATENT DOCUMENTS

| 5,849,011 | A | * | 12/1998 | Jones et al. .................... 606/47 |
| 5,964,791 | A | * | 10/1999 | Bolmsjo ...................... 607/100 |
| 6,035,238 | A | | 3/2000 | Ingle et al. |
| 6,044,847 | A | | 4/2000 | Carter et al. |
| 6,081,749 | A | | 6/2000 | Ingle et al. |
| 6,091,995 | A | | 7/2000 | Ingle et al. |
| 6,139,569 | A | | 10/2000 | Ingle et al. |
| 6,156,060 | A | | 12/2000 | Roy et al. |
| 6,216,704 | B1 | | 4/2001 | Ingle et al. |
| 6,236,891 | B1 | | 5/2001 | Ingle et al. |
| 6,241,702 | B1 | * | 6/2001 | Lundquist et al. ............ 604/22 |
| 6,254,598 | B1 | * | 7/2001 | Edwards et al. .............. 606/41 |
| 6,283,987 | B1 | | 9/2001 | Laird et al. |
| 6,292,700 | B1 | | 9/2001 | Morrison et al. |
| 6,322,584 | B2 | | 11/2001 | Ingle et al. |
| 6,325,798 | B1 | | 12/2001 | Edwards et al. |
| 6,413,255 | B1 | | 7/2002 | Stern |
| 6,416,504 | B2 | | 7/2002 | Mosel et al. |
| 6,461,332 | B1 | | 10/2002 | Mosel et al. |
| 6,629,535 | B2 | * | 10/2003 | Ingle et al. ................. 128/898 |
| 2001/0014819 | A1 | | 8/2001 | Ingle et al. |
| 2001/0018606 | A1 | | 8/2001 | Ingle et al. |
| 2002/0111586 | A1 | | 8/2002 | Mosel et al. |

OTHER PUBLICATIONS

Fulmer, B.R. et al., *Acute and Long–Term Outcomes of Radio Frequency Bladder Neck Suspension*, J. Urology, 167:141–145, (2002).

SURx® Press Release, *SURx® Expands Radio Frequency Product Family with New Transvaginal System for Urinary Incontinence*(Mar. 22, 2002) 2 pages total.

SURx® Press Release, *SURx® Receives FDA Clearance to Market Radio Frequency Bladder Neck Suspension Treatment for Female Urinary Incontinence*(Jan. 29, 2002) 2 pages total.

SURx®, Rencent Newshttp;://surx.com/index.cfm-?SCREEN=surx&page,=abNews (© 2001) printed from web Aug. 14, 2002, 2 pages total.

* cited by examiner

*Primary Examiner*—Roy D. Gibson
(74) *Attorney, Agent, or Firm*—Townsend and Townsend and Crew LLP

(57) ABSTRACT

Methods and devices for improving contact between tissue and a probe. In exemplary embodiments, methods of the present invention include a deploying a needle into a target tissue and retracting the needle so that tenting around the needle is reduced. The retracting of the needle can increase the amount of tissue contact between a surface of the tissue and a surface contacting portion of a probe body.

62 Claims, 18 Drawing Sheets

|  | RETRACTED POSITION | DEPLOYED POSITION | PARTIALLY DEPLOYED POSITION | |
|---|---|---|---|---|
| PORT 154 | P | E | P | E |
| PORT 156 | E | P | E | P |
| PORT 158 | P | E | E | P |
| PORT 160 | E | P | P | E |

NEEDLE DEPLOYMENT FOR TEMPERATURE SENSING FROM AN ELECTRODE

CROSS-REFERENCES TO RELATED APPLICATIONS

The present application is related to U.S. patent application Ser. No. 09/991,368, filed Nov. 20, 2001 and U.S. patent application Ser. No. 10/102,596, filed Mar. 19, 2002, the complete disclosures of which are incorporated herein by reference.

The present application is also related to commonly owned U.S. Pat. Nos. 6,035,238, 6,044,847, 6,091,995, 6,156,060, 6,139,569, 6,216,704, 6,236,891, 6,283,987, and 6,292,700, the complete disclosures of which are also incorporated herein by reference.

BACKGROUND OF THE INVENTION

The present invention generally relates to medical devices, methods, and systems. More specifically, the present invention provides techniques for improving and monitoring the selective delivery of a heating energy to tissues to cause tightening, shrinking, and/or debulking, particularly for the noninvasive treatment of urinary incontinence and hernias, for cosmetic surgery, and the like.

Urinary incontinence arises in both women and men with varying degrees of severity, and from different causes. In men, the condition occurs most often as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Unfortunately, each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

One proposed alternative method for treatment of urinary incontinence is described in commonly owned U.S. Pat. No. 6,216,704 B1. The proposed method of treating urinary incontinence includes heating and shrinking fascia and other collagenous support tissue in a non-invasive manner to cause the tissue to contract, while minimizing substantial necrosis of adjacent, intermediate tissues. In some embodiments, a plurality of cooled electrodes are used to cool the intermediate tissue and to deliver the heating energy to the target tissue. To monitor the temperature of the target tissue and the surrounding tissue, a temperature sensing needle may be advanced into the tissue.

While the proposed treatment is high effective, unfortunately, in some instances, insertion of the needle causes a surface of the tissue around the needle to "tent" and such that the tenting region loses contact with the cooled electrodes. Because the tissue is not contacting the cool surfaces, the tented tissue may be burned and damaged.

For the above reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods and devices which reduce the damage to the surrounding tissue.

BRIEF SUMMARY OF THE INVENTION

The present invention provides methods and probes for monitoring a temperature of a target tissue and for improving contact between a tissue contacting surface of the probe and the tissue surface.

The probes of the present invention generally include a probe body that carries at least one electrode on a tissue contacting surface of the probe. To selectively heat the target tissue, while minimizing necrosis to tissue between the target tissue and the electrode(s) and probe body, the tissue contacting surfaces can be cooled with a cooling assembly. This cooling maintains a cooled tissue on and between each electrode below a maximum safe tissue temperature, typically being below about 45° C.

The therapeutic heating and cooling provided by the electrodes of the present invention will often be verified and/or controlled by directly sensing the temperature of the target tissue and the adjacent tissue. Such temperature sensing may be provided by using temperature sensors on the probe or by inserting a needle containing at least one temperature sensor into the target tissue.

The temperature sensing needle may be affixed to or advanceable from a probe supporting the electrode adjacent to or between the electrode segments. Typically, a controller will provide signals to the cooling assembly and the electrodes so that the electrodes and other cooling surfaces continually chill the engaged tissue while the RF current is continuously delivered, pulsed, or otherwise delivered to increase the temperature of the treatment zone incrementally, preferably in a step-wise manner, until it reaches a temperature of 60° C. or more, while at the same time limiting heating of the intermediate and other surrounding tissue to 45° C. or less, per the feedback from the needles.

It has been found, however, that insertion of the needle into the tissue may cause a tenting region to form around the needle such that a portion of the tissue surface loses contact with the tissue contacting surface of the probe. To reduce, and preferably eliminate the tissue tenting region, the needle can be partially retracted from its deployed position so as to reduce the tissue deformation around the needle and to increase the amount of tissue contacting the cooled tissue contacting surface of the probe. In exemplary embodiments the needle can be deployed between approximately 10 mm and 20 mm along the needle axis and thereafter retracted between about 6 mm and 11 mm along the needle axis to reduce the tenting region. It should be appreciated however, that in other embodiments, the needle can be deployed different distances and retracted different distances, and the present invention should not be limited to the ranges described herein.

In exemplary embodiments, there are three stages of needle deployment. In a first stage, a needle is in a retracted position within a probe body. In a second stage, the needle is deployed beyond the intended treatment depth. In such a position, there is typically some tissue tenting which causes the tissue that immediately surrounds the needle to not contact the cooled surfaces of the probe tip (e.g., cooled electrodes and/or other cooling surfaces). In a third stage, the needle is in a partially retracted position so as to position the needle in a proper treatment depth. The needle in the partially retracted position reduces the amount of tissue tenting and increases the amount of contact between the tissue surface and the cooling surfaces (e.g., cooled electrodes and/or probe cooling surfaces). Thus, there is less damage to the tissue surrounding the target tissue.

In one aspect, the present invention provides a method of inserting a needle into tissue. The needle is moved from a retracted position to a deployed position. The needle can then be retracted to a partially deployed position to reduce a tissue tenting in the tissue around the needle.

In a further aspect, the present invention provides a method for improving contact with a surface of a tissue. The method includes placing a tissue contacting surface of a probe body against the surface of the tissue. The tissue contacting surface can include at least one of cooled electrodes, a cooled portion of the probe body, a temperature sensor on the probe body, an uncooled portion of the probe body, or the like. A needle can be deployed into the tissue. Thereafter, the needle can be partially retracted to increase the amount of contact between the tissue contacting surface of the probe body and the surface of the tissue. The increasing of the amount of contact is preferably carried out through a reduction (or elimination) of a tenting region around the needle.

In a further aspect, the present invention provides a device for treating a target tissue. The device comprises a body having a tissue contacting surface that contacts the tissue surface. A needle is movably coupled to the body. The needle comprises a tip that is movable from a retracted position to a deployed position. The needle tip can be moved from the deployed position and locked into a partially retracted position.

In another aspect, the present invention provides a probe for treating a target tissue that is below a tissue surface. The device comprises a body having at least one electrode attached to the body. A needle can be coupled to the body, in which the needle is movable from a retracted position to a deployed position to a partially retracted position. In the deployed position, a tip of the needle is typically deployed beyond the target tissue. In the partially retracted position, the needle is retracted from the deployed position such that the needle tip is positioned adjacent (e.g., within) the target tissue. Retraction of the needle can increase the amount of surface contact between the tissue surface and the electrode(s) and reduce any tissue tenting around the needle. In exemplary embodiments, a tissue contacting surface is coupled to a cooling assembly that cools the tissue contacting surface of the electrode(s).

In another aspect, the present invention provides a system for treating a target tissue of a patient body. The system comprises a probe body comprising a proximal portion and a distal portion. A plurality of electrodes can be positioned on the distal portion of the probe body. A power source, such as a high frequency RF source, is coupled to the plurality of electrodes for delivering an energy to the tissue through the electrodes. The system can include a needle that is coupled to actuation means that move the needle between a first position, a second position, and a third position. In the first position, the needle is housed within a distal portion of the probe body. In the second position, a tip of the needle is extended beyond the target tissue. In the third position, the needle is retracted from the second position such that the needle tip is positioned in the target tissue.

For a further understanding of the nature and advantages of the invention, reference should be made to the following description taken in conjunction with the accompanying drawings and claims.

DETAILED DESCRIPTION OF THE INVENTION

Figure 1:
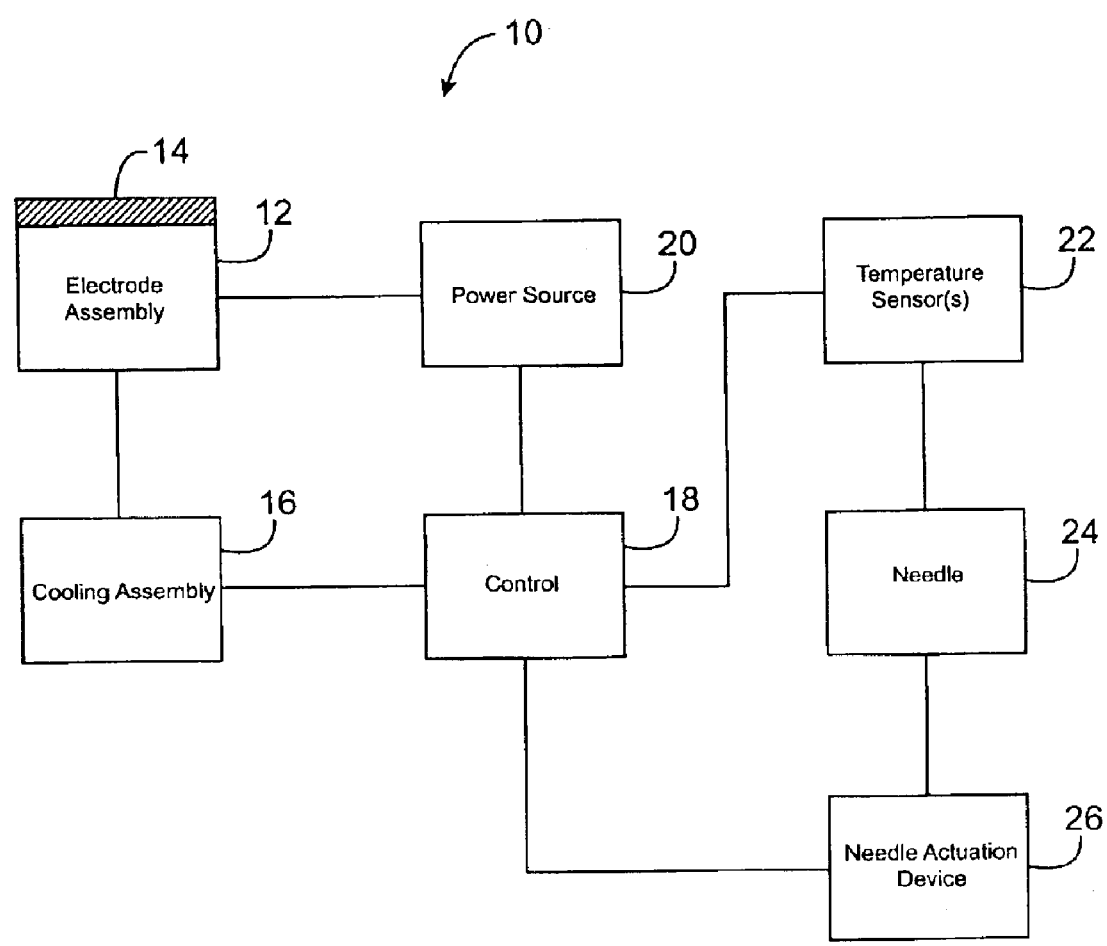
FIG. 1 schematically illustrates a simplified system of the present invention.

The present invention relates to improving the controlled shrinkage or contraction of a support tissue of the body, typically fascia or other collagenated tissue. For treatment of urinary incontinence, the tissue structure will be one that is responsible in some manner for control of urination, or for supporting a such a tissue. Exemplary tissue structures include the urethral wall, the bladder neck, the bladder, the ureter, bladder suspension ligaments, the sphincter, pelvic ligaments, pelvic floor muscles, fascia, and the like. Treatment of other conditions may be effected by selective shrinking of a wide variety of other tissues, including (but not limited to) the diaphragm, the abdominal wall, the breast supporting ligaments, the fascia and ligaments of the joints, the collagenated tissues of the skin, and the like.

Tissue contraction results from controlled heating of the tissue by affecting the collagen molecules of the tissue. Contraction occurs as a result of heat-induced uncoiling and repositioning of the collagen (beta) pleated structure without substantial collateral tissue damage.

The temperature of the target tissue structure will generally be raised to a value in the range from about 60° C. to 110° C., often being in the range from about 60° C. to 80° C., and will generally effect a shrinkage of the target tissue in at least one dimension of between about 15 and 50 percent. In many embodiments, heating energy will be applied for a period of from 30 seconds to 5 minutes. These heating times will vary depending on the configuration of the electrodes, power source, target tissue, and the like. One exemplary method of controlling heating of the tissue is described in co-pending U.S. patent application Ser. No. 10/102,596, filed Mar. 19, 2002, the complete disclosure of which is incorporated herein by reference.

The rise in temperature may be quite fast, although there will often be advantages in heating tissues more slowly, as this will allow more heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy.

The total amount of energy delivered will depend in part on which tissue structure is being treated, how much tissue is disposed between the target tissue and the heating element, and the specific temperature and time selected for the protocol. The power delivered will often be in the range from 10 W to 100 W, usually being about 30 W. The temperature will usually not drop instantaneously when the heating energy stops, so that the tissue may remain at or near the therapy temperature for a time from about 10 seconds to about 2 minutes, and will often cool gradually back to body temperature.

To reduce collateral damage to the tissue in between the target tissue and the electrodes (referred to herein as "intermediate tissue"), the methods and probes of the present invention can deliver the heating energy through electrodes having a cooled tissue contacting surface. The cooled surfaces of the electrodes and probe body can contact the tissue surface to cool the intermediate tissue so as to prevent excessive heating to the non-target intermediate tissue.

In exemplary embodiments, a temperature of the target tissue and/or the intermediate tissue can be monitored during the delivery of energy. The temperature of the target tissue can be monitored with one or more temperature sensors on the probe body and/or a needle assembly carrying one or more temperature sensors. It should be appreciated however, that in other embodiments, instead of temperature sensors, the needle can carry other sensors to monitor other characteristics of the tissue.

The needle assembly can be configured to be deployed a specified distance and thereafter be partially retracted to reduce an effect, herein referred to as tissue tenting. Tissue tenting is used to refer to a deformation of the tissue region around the needle that, due to frictional forces from the insertion of the needle into the tissue, is moved off of the tissue contact surface of the probe. Because the tissue tenting region is not contacting the cooling surfaces of the probe (e.g., electrodes or probe body surfaces), the tissue region in the tenting region may be burned.

While the remaining description is generally directed at probes and methods of improving the treatment for urinary stress incontinence of a female patient by measuring a temperature of the target zone with a tissue sensor, it will be appreciated that the present invention will find many other applications for selectively directing therapeutic heating energy into the tissues of a patient body for shrinking of tissues, for ablation of tissues and tumors, and the like.

FIG. 1 schematically illustrates a system 10 of the present invention. System 10 includes an electrode assembly 12 that includes an electrode tissue contacting surface 14. Electrode assembly 12 can include one or more individual electrodes and can be positioned on a probe body (not shown). A cooling assembly 16 can be coupled to the electrode assembly 12 and a control or controller 18 so as to cool electrode tissue contacting surface 14 and other tissue contacting surfaces of probe body. Controller 18 can be coupled to a power source 20 and electrode assembly 12 to control the delivery program of energy into a target tissue. System 10 can also include a temperature sensor 22 that is coupled to controller 18 and coupled to the probe body. In other embodiments, however, temperature sensor 22 can be part of an assembly that is separate from the probe body.

In exemplary embodiments, at least one temperature sensor 22 can be positioned on a needle 24, such as a nitinol needle, that is deployable from the probe body. If temperature sensor 22 is attached to needle 24, system 10 can include a needle deployment device 26 to deploy the needle from a retracted position to a deployed position. Additionally or alternatively, temperature sensor(s) 22 can be attached directly to the probe body so as to measure the temperature of the surface of the tissue.

Figure 2:
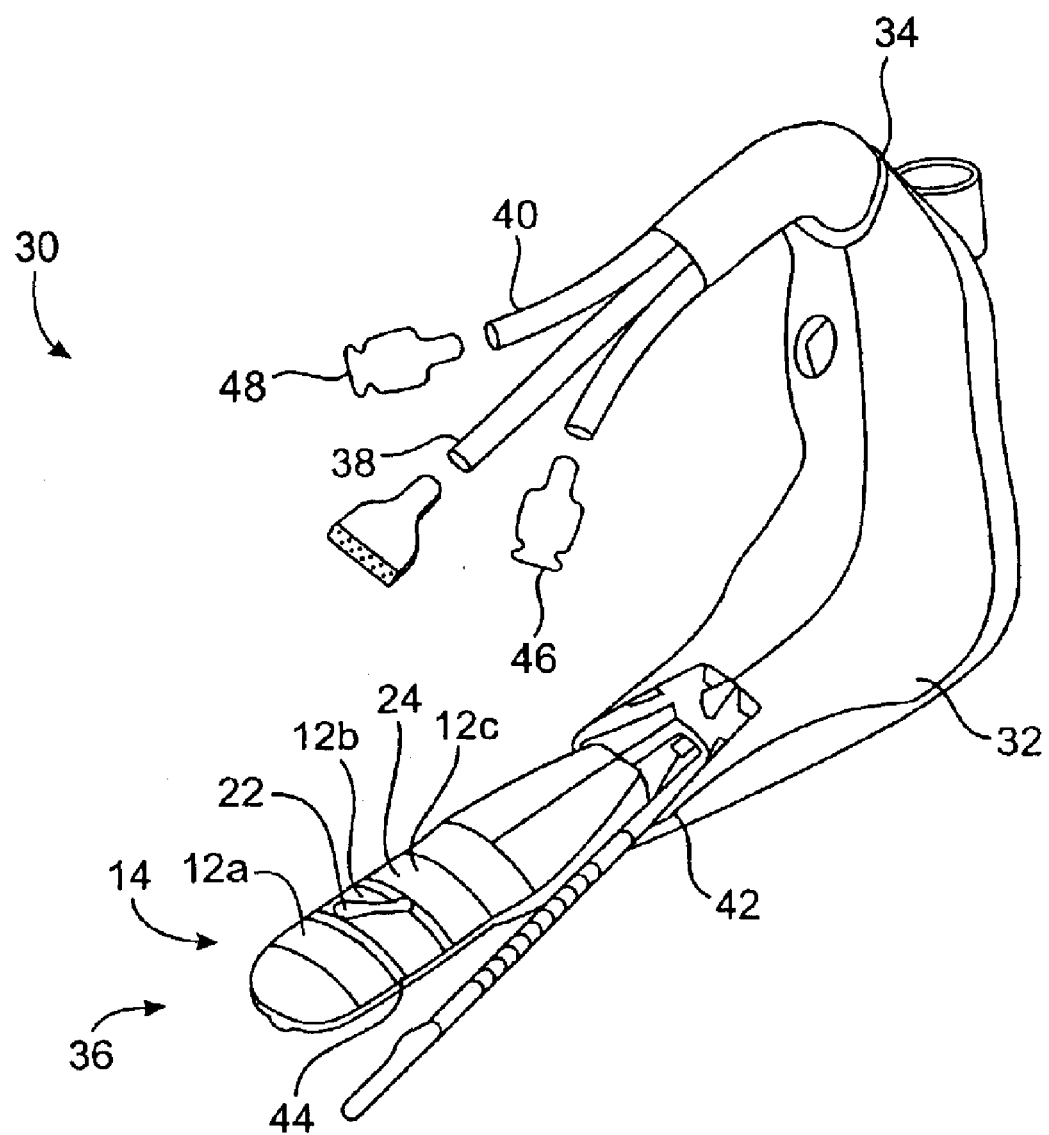
FIG. 2 illustrates one exemplary probe of the present invention.

FIG. 2 illustrates one exemplary probe 30 of the present invention. The device generally includes a probe body 32 having a proximal end 34 (e.g., handle) and a distal end 36 (e.g., probe tip). A plurality of electrodes 12 can be attached to distal end 36 of probe body 32 to deliver an electrical energy to a target tissue. In the illustrated embodiment, there are three electrodes 12a, 12b, 12c that are coupled to a high frequency power source (e.g., RF energy, microwave or the like) and/or controller 18 through connector 38.

In some embodiments, probe 30 can include a urethral guide assembly 42 to assist in positioning electrodes 12 adjacent the target tissue within the patient's body. A more complete description of urethral guide assembly 42 can be found in co-pending and commonly owned U.S. patent application Ser. No. 09/991,368, filed Nov. 20, 2001, the complete disclosure of which is incorporated herein by reference.

Probe body 32 can also carry needle 24 for deployment into the patient's tissue. Needle 24 typically carries a temperature sensor 22. It should be appreciated, however, that needle 24 can carry an electrode, or the needle can be used for delivering a medicant, pharmacological agents, saline, fluids to enhance energy delivery, or the like.

A more complete description of some exemplary probes that can carry the needle 24 of the present invention are described in commonly owned U.S. Pat. Nos. 6,035,238, 6,044,847, 6,091,995, 6,156,060, 6,139,569, 6,216,704, 6,236,891, 6,283,987, and 6,292,700, the complete disclosures of which are incorporated herein by reference.

To selectively heat a target tissue, while minimizing necrosis to tissue between the target tissue and the electrodes (e.g., intermediate tissue), electrode surfaces 14 and other tissue contacting surfaces of the probe can be cooled with cooling assembly 16. (FIG. 1). This cooling maintains a cooled tissue region on and around each electrode below a maximum safe tissue temperature, typically being below about 45° C. Cooling assembly 16 will typically include at least one conduit 40 through electrode(s) 12 for a circulation of a cooling fluid, but may optionally rely on thermoelectric cooling or the like. A temperature of electrode surface 14 may be regulated by varying the temperature and/or flow rate of the cooling fluid with controller 18. Cooling may also be provided through the use of an ice bath, by endothermic chemical reactions, by standard refrigeration mechanisms, or the like. Ideally, cooling assembly 16 cools an area which extends beyond the energized electrode surfaces to prevent the formation of any hot spots adjacent the tissue surface, and to maximize the heat removal from intermediate tissue without chilling it to or below temperatures that irreversibly damages the tissue, such as might occur when freezing the tissue.

Electrode assembly 12 of the present invention will generally include a series of conductive surface segments which are aligned to define a substantially flat electrode surface. The electrode surface segments can be separated by an electrically insulating material, with the insulation being much smaller in surface area than the conductive segments. Typically, there will be between one and eight electrodes, which are separated by a distance of between about 0.25 mm and 1.0 mm.

In some embodiments, however, electrodes 12 may be rounded and/or covered by an insulating material to prevent concentrations of the electrical potential and injury to the engaged tissue surfaces.

In the embodiment illustrated in FIG. 2, electrode assembly 12 includes electrodes 12a, 12b, 12c, each of which is electrically isolated from the other electrodes through an electrically insulative and thermally conductive space 44. This allows each of the electrodes to be individually energized so as to selectively deliver heating energy to a specific portion of the target tissue. Conduit 40 defines a flow path between a cooling inflow port 46 and a cooling outflow port 48. Electrodes 12a, 12b, and 12c may comprise surfaces of separated segments of aluminum, gold plated brass, gold plated copper, stainless steel, or the like.

It should also be understood that while electrode assembly 12 of the present invention is generally herein described with reference to a linear array geometry, the present invention also encompasses electrodes which are segmented into two-dimensional arrays, electrodes that are rotatable, non-linear electrode assemblies, curved electrodes, ribbed electrodes, or the like. Where opposed sides of the tissue are accessible for relatively large array structures, such as along the exposed skin, or near the major cavities and orifices of the body, the electrode surfaces will preferably be separated by a gap which is less than a width (and length) of the electrodes.

For example, in some embodiments, one electrode structure may be disposed within a large body cavity such as the rectum or vagina, while the other is placed in an adjacent cavity, or on the skin so that the region to be treated is between the electrode surfaces. In other embodiments, one or both electrodes may be inserted and positioned laparoscopically. It will often be desirable to clamp the tissue tightly between the electrodes to minimize the gap therebetween, and to promote efficient coupling of the electrode to the tissue.

In exemplary embodiments, electrodes 12a, 12b, 12c, are energized by a radiofrequency (RF) power source 20. Multiplexers (not shown) can be used with controller 18 to individually energize each electrode segment, typically varying the power or time each segment is energized to more nearly uniformly heat fascia or other target tissue. The use of a radiofrequency current of relatively low voltage, helps to avoid arcing and damage to tissue in direct contact with electrodes 12. Generally, sufficient heating can be provided by a current of between about 0.2 amps and 2.0 amps, preferably about 1.0 amp, and a maximum voltage of between about 30 and 100 volts rms., preferably being about 60 volts rms. Each electrode will often have a surface area of between about 0.5 cm$^2$ and 200 cm$^2$, and the current density in the target tissue will often be between about 1 mA/cm$^2$ and 4 A/cm$^2$, preferably being between about 5 mA/cm$^2$ and 500 mA/cm$^2$. This can provide a maximum power in the range from about 10 W to about 200 W, often being about 30 W. Using such low power settings, if electrode 12 is lifted away from the intermediate tissue, there will typically be no arcing. Instead, the current will simply stop. This highlights the difference between the electrical tissue heating of the present invention and other conventional electrosurgical techniques.

The therapeutic heating from electrode assembly 12 and cooling provided by cooling assembly 16 of the present invention will often be verified and/or controlled by sensing the temperature of the target tissue and the tissue surface with temperature sensor(s). Controller 18 will typically include a processor that can run a computer algorithm or program to direct the application of cooling flow and RF power through electrode assembly 12, typically based at least in part on a temperature signal sensed by temperature sensors 22.

Such temperature sensing may be provided using temperature sensors positioned on the distal end 36 of the catheter body (not shown) and/or needle 24 that carries one or more temperature sensors 22. Temperature sensor 22 may sense the temperature of the electrodes, the target tissue, the tissue at the tissue/electrode interface, and/or the intermediate tissue.

In some exemplary embodiments, needle 24 carries a temperature sensor 22 at or near its tip such that when the tip of needle 24 is positioned within the target tissue, the controller will be able to monitor the temperature of the target tissue during the procedure. Temperature sensors 22 will preferably continuously sense the tissue temperature during the procedure. Temperature sensors 22 may comprise thermistors, thermocouples, or the like.

In some exemplary embodiments needle 24 can carry two or more temperature sensors. In typical configuration needle 24 carries one sensor at the tip to be positioned at or near a center of the target tissue, and a second sensor along the shaft of the needle so as to be positioned at an edge of the desired protection zone. Thus, the second sensor can be placed in the intermediate tissue while the first sensor can be in the target tissue. In other methods of using such embodiments, the needle can be deployed beyond the target zone and partially retracted to a position such that the needle tip is still beyond the target zone. In such a position, the temperature sensor at the tip can monitor the temperature of tissue 210 beyond the target zone (FIG. 10) while the temperature sensor along the shaft can measure the temperature of the target zone.

In yet further embodiments, needle 24 can carry more than two temperature sensors. In one exemplary configuration, needle 24 can carry a first sensor at the tip and the second and third sensors along the shaft. In some methods, the first sensor can monitor tissue 210 beyond the target zone, while the second sensor can monitor tissue in the target zone, while the third sensor can monitor the intermediate tissue. In other methods, however, the first sensor can be positioned in the target zone while the second and third sensors can be positioned at different points in the intermediate tissue.

The temperature sensing needle may be affixed to or advanceable from a probe supporting the electrodes or the temperature sensing needle may be completely separate from probe body 32. Alternatively, two or more separate needles may be used. Typically, controller 18 will provide signals to cooling system 16 and the electrodes so that the electrodes chill the engaged tissue continually while the RF current is pulsed or otherwise delivered to increase the temperature of the treatment zone incrementally, ideally in a step-wise manner, until it reaches a temperature of 60° C. or more, while at the same time limiting heating of the intermediate tissue to 45° C. or less per the feedback from the needles.

Figure 3:
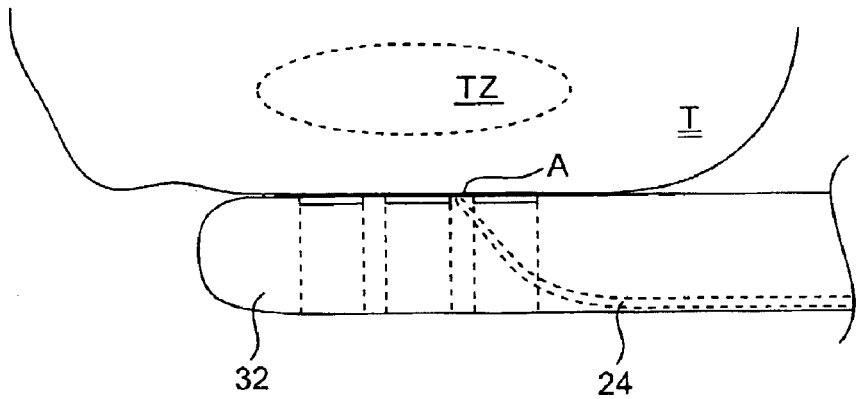
FIG. 3 is an enlarged elevational view of a distal end of a probe of the present invention in which the temperature sensing needle is in a retracted position.
Figure 4:
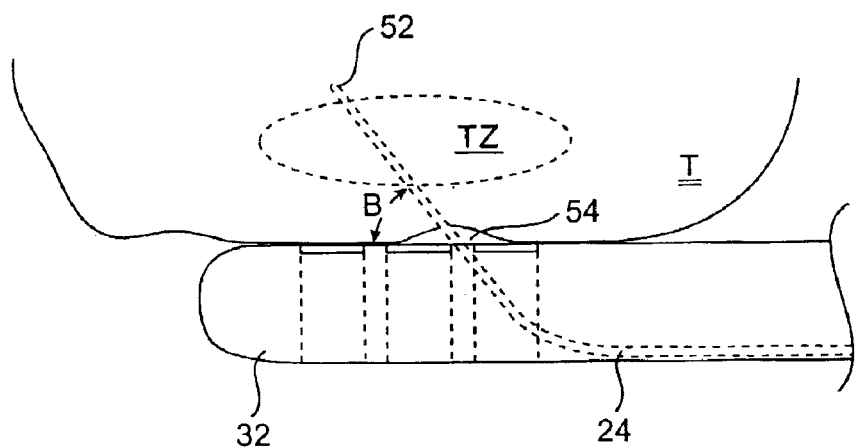
FIG. 4 is an enlarged elevational view of a distal end of a probe of the present invention in which the temperature sensing needle is in an extended, deployed position.
Figure 5:
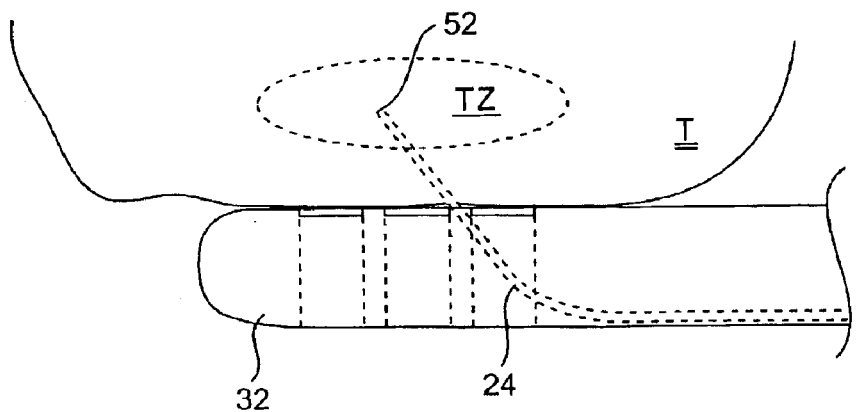
FIG. 5 is an enlarged elevational view of a distal end of a probe of the present invention in which the temperature sensing needle is in a partially retracted position.

FIGS. 3 to 5 illustrate one exemplary needle 24 that carries a temperature sensor 22. As shown in FIG. 3, during delivery to the target site, needle 24 will typically be positioned in a fully retracted position within probe body 32.

Once at the target site, needle 24 can be activated to exit probe body 32 through an aperture A. A tip 52 of needle 24 can carry the temperature sensor (not shown for clarity) which can be in communication with controller 18 through a lead that runs down an inner lumen (not shown) of needle 24.

As shown in FIG. 4, once a tissue contacting surface of probe 32, typically at least electrode surfaces 14, is contacted against tissue T, the user can activate a needle actuation device (FIG. 1) to move the needle from its retracted position to a fully deployed position. In the illustrated embodiment, needle 24 is deployed at an angle (beta) from electrode surface 14 an into tissue T. It should be appreciated that while the needle is illustrated as being deployed in a non-orthogonal angle from electrode surface, that in some embodiments, needle 24 can be deployed at an orthogonal angle relative to electrode surface 14.

In exemplary embodiments, needle tip 52 in a deployed position (FIG. 4) will typically be positioned beyond a target tissue zone TZ. As shown, deploying of the needle into tissue T may cause a tissue tenting region 54 directly around needle 24 due to the frictional forces of the needle entering tissue T. While tissue T does relax after the initial deployment of needle 24, a tenting region 54 in the tissue still remains. Such tenting of the tissue causes tenting region 54 to lose contact with the cooled electrodes or other cooling surfaces, and if energy is delivered through tissue T, tissue in tenting region 54 will likely be damaged.

To reduce the size of tenting region 54 and to preferably completely eliminate tenting region 54, needle 24 can be partially retracted from the deployed position. Frictional forces from the retraction of the needle has been found to retract tenting region 54 so that the tissue surface around the needle is moved back into contact with a cooled tissue contacting surface of the probe (e.g., electrode surface 14). Consequently, the amount of tissue that contacts the tissue contacting surface is increased, and the amount of damage to the tissue surface during heating can be reduced, and preferably eliminated. In exemplary configurations in the partially retracted position, needle tip 52 (and temperature sensor 22) is positioned within target zone TZ so as to allow temperature sensor to monitor the temperature of the target zone tissue.

It should be appreciated however, to further reduce or prevent tenting it may be possible to use a needle material that would have less friction with the tissue, or possibly to coat the needle with PTFE (i.e., Teflon®), or other material that reduces the friction between the needle and the tissue.

Figure 6A:
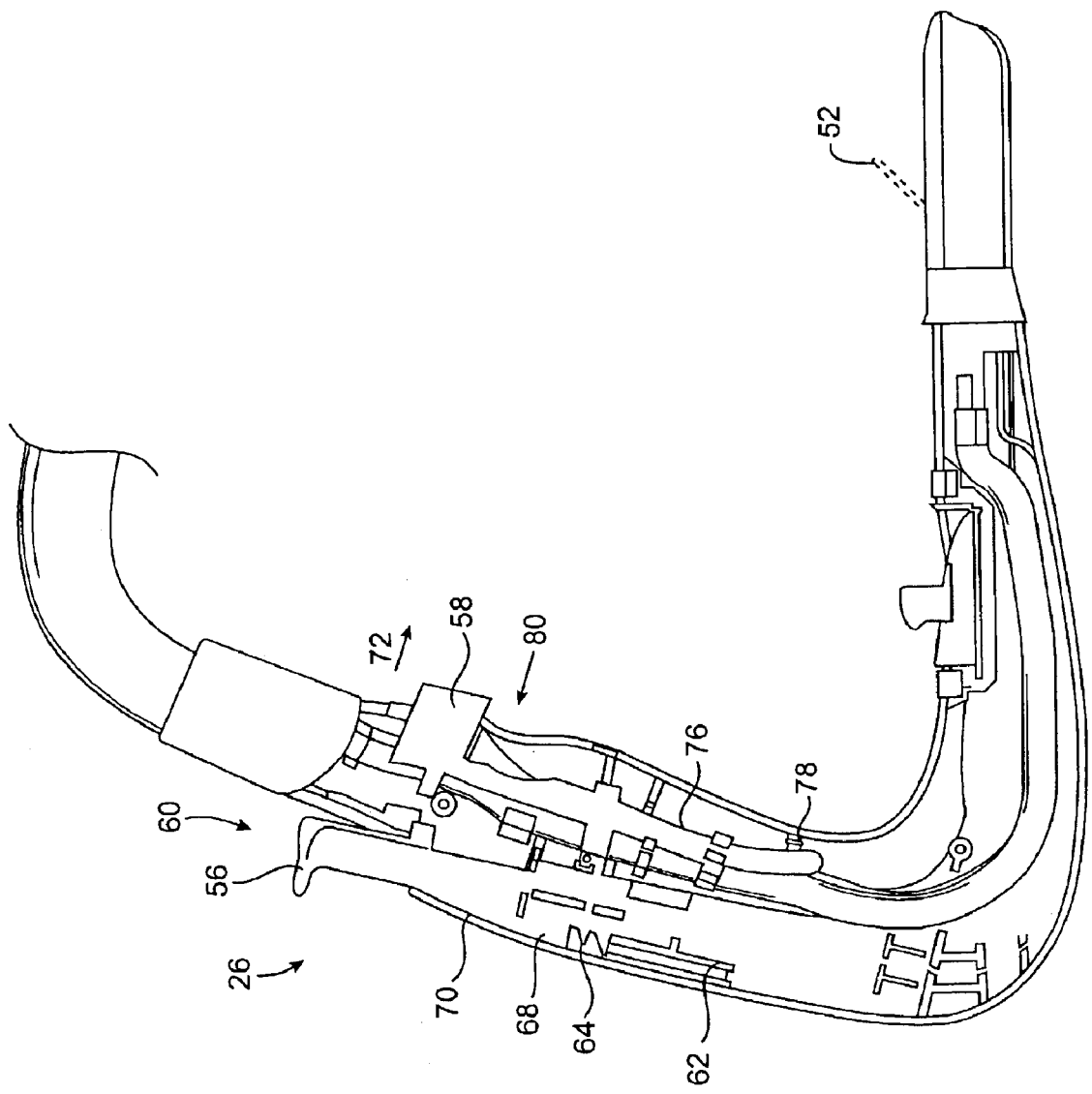
FIG. 6A is a cut away elevational view of a probe having a manual needle actuation device that has a plunger and release.

FIGS. 6A to 7 illustrate some exemplary needle actuation devices 26 that can be used to deploy and retract the needle and temperature sensors. It should be appreciated however, that the illustrated embodiments are merely examples and should not limit the scope of the present invention. A variety of other conventional and proprietary needle actuation devices can be used to deploy and retract the needles of the present invention.

Figure 6B:
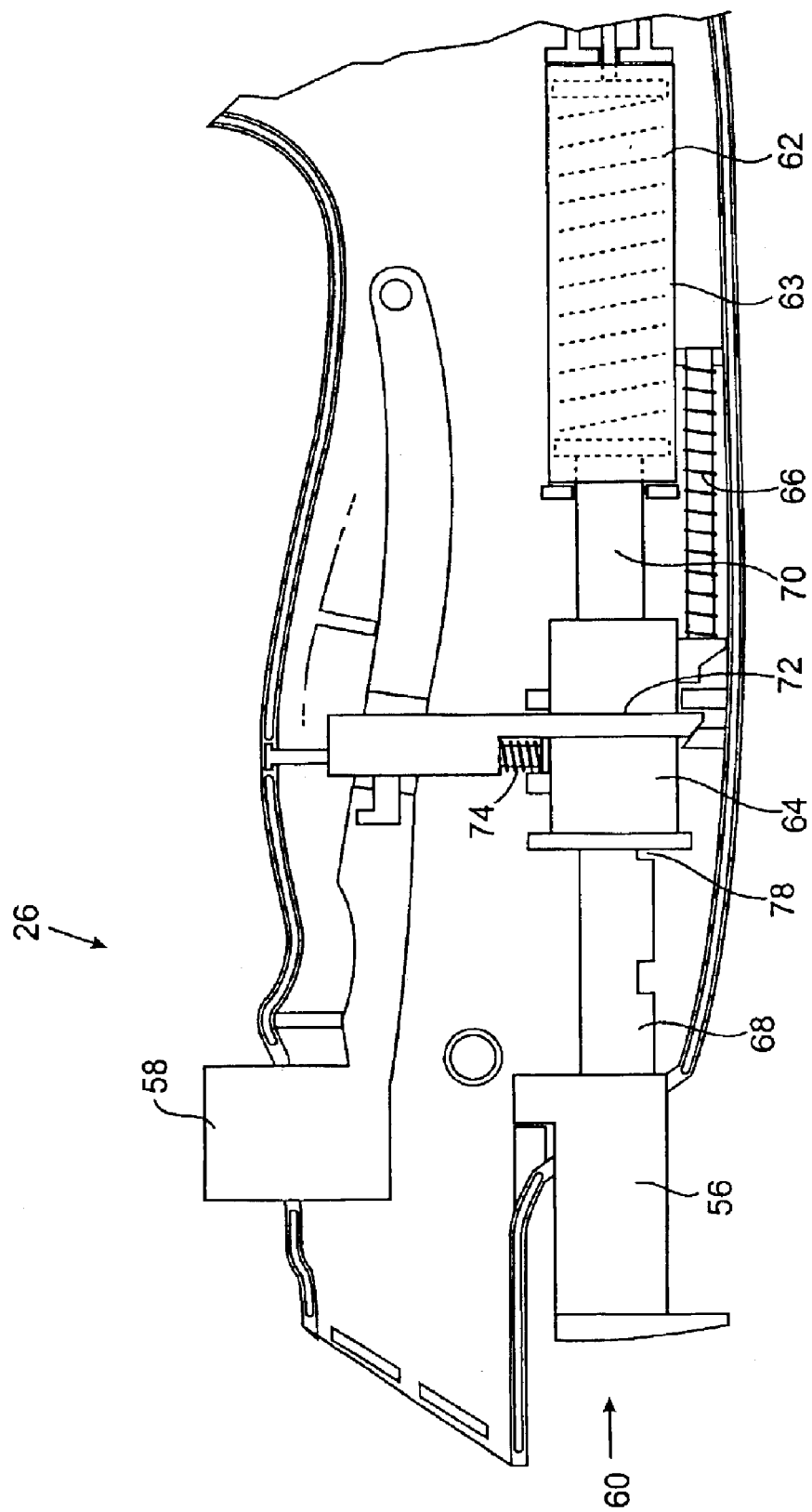
FIG. 6B is a close-up cut away elevational view of a proximal portion of the probe of FIG. 6A in which the plunger assembly and needle assembly are in a retracted position.

FIGS. 6A to 6F illustrate a probe 30 having one exemplary manually actuatable needle actuation device. Needle actuation device 26 includes a plunger assembly 56 and a release assembly 58 that control the locking (e.g., deployment) and unlocking (e.g. retraction) of needle 24. As illustrated in FIGS. 6A and 6B, plunger assembly 56 can be biased with at least one main spring coil 62 that is housed within a spring support housing 63 so as to bias trigger or plunger 56 in an uncompressed position and needle 24 in a first, retracted position.

Figure 6C:
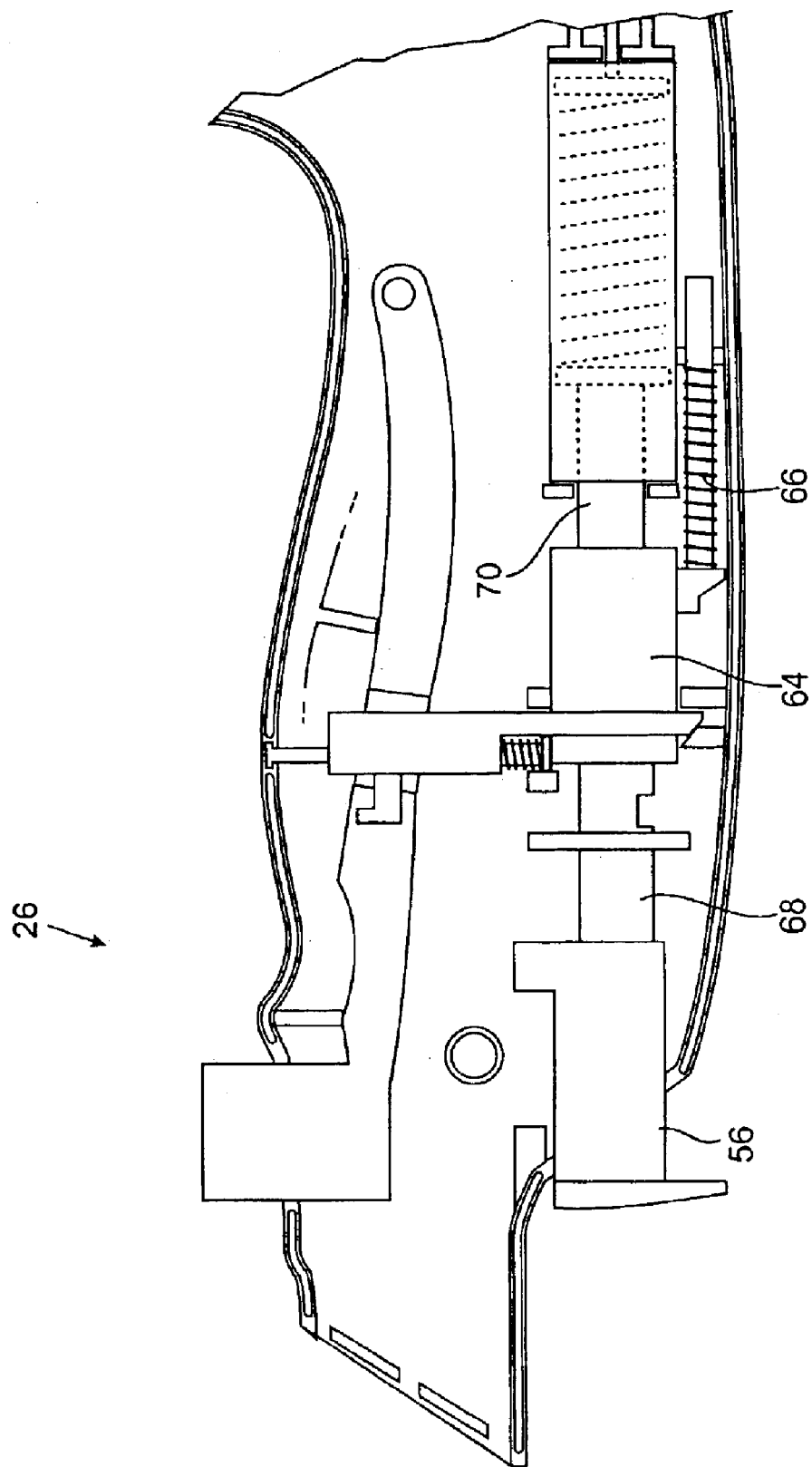
FIG. 6C is a close-up cut away elevational view of the proximal portion of probe of FIG. 6A in which the plunger assembly is at a middle of deployment of the needle.

To begin deployment, an operator can grasp a grip of probe 30 in the palm of the hand and move plunger 56 in a direction of arrow 60 with a thumb to overcome the biasing force of main spring coil 62. Movement of plunger 56 causes needle 24 to move from an initial retracted position to a deployed position. (FIGS. 3 and 4). As shown in FIG. 6C, movement of plunger 56 and main spring 62 to a semi-compressed position moves needle 24 toward its deployed position. During an initial portion of the travel of plunger 56, a lock guide 64 is maintained in position under a biasing force of a lock guide spring 66 over a connector body 68 that is coupled to plunger 56.

Once needle 24 is deployed a predetermined distance, lock guide 64 is engaged by a sleeve body 70. Once lock guide 64 engages sleeve body 70, lock guide 64 moves with needle 24, typically until a maximum travel is achieved. (FIG. 6C).

Figure 6D:
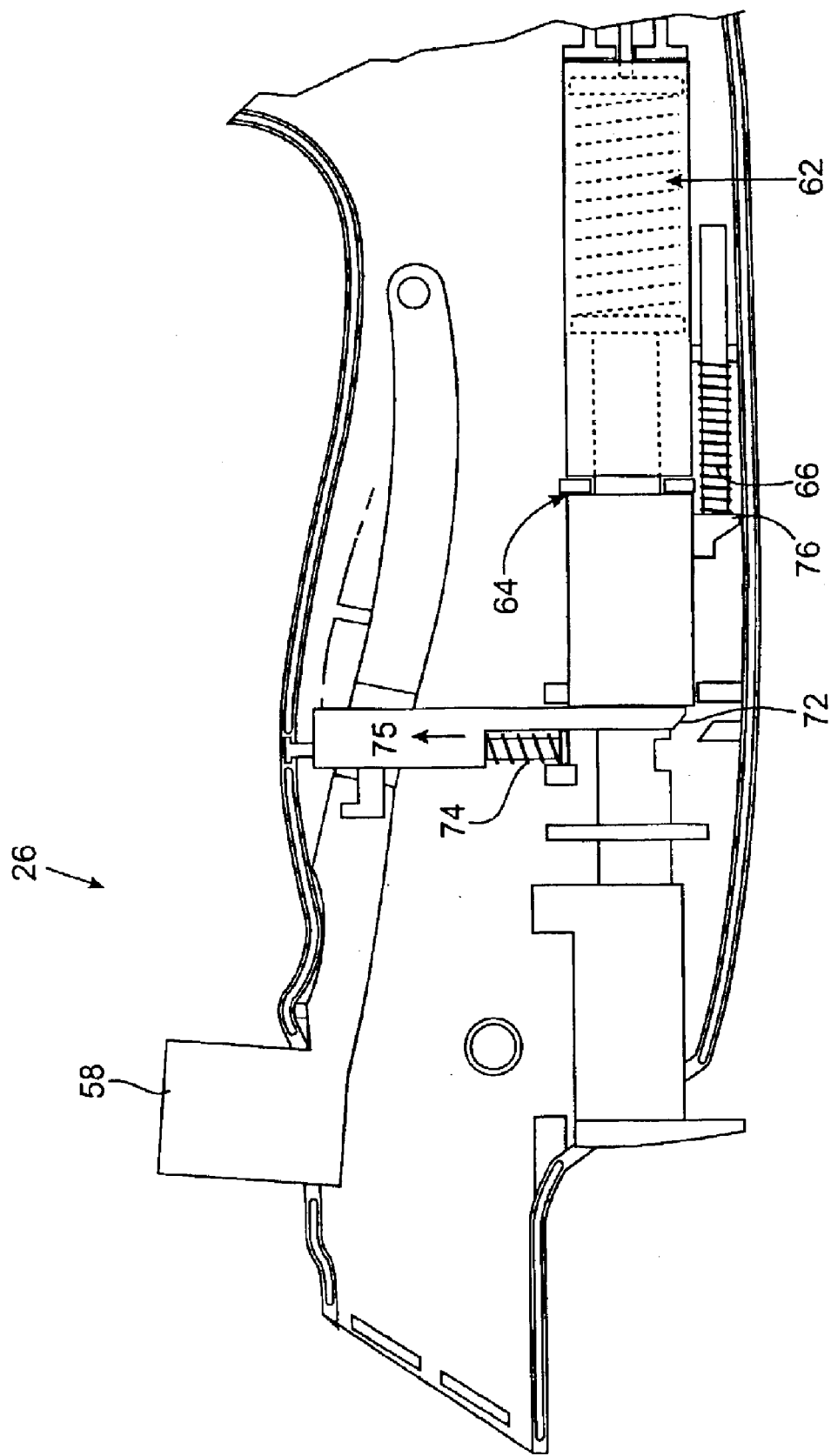
FIG. 6D is a close-up cut away elevational view of the proximal portion of the probe of FIG. 6A in which the plunger assembly is in a compressed configuration and the needle is in a deployed position.
Figure 6E:
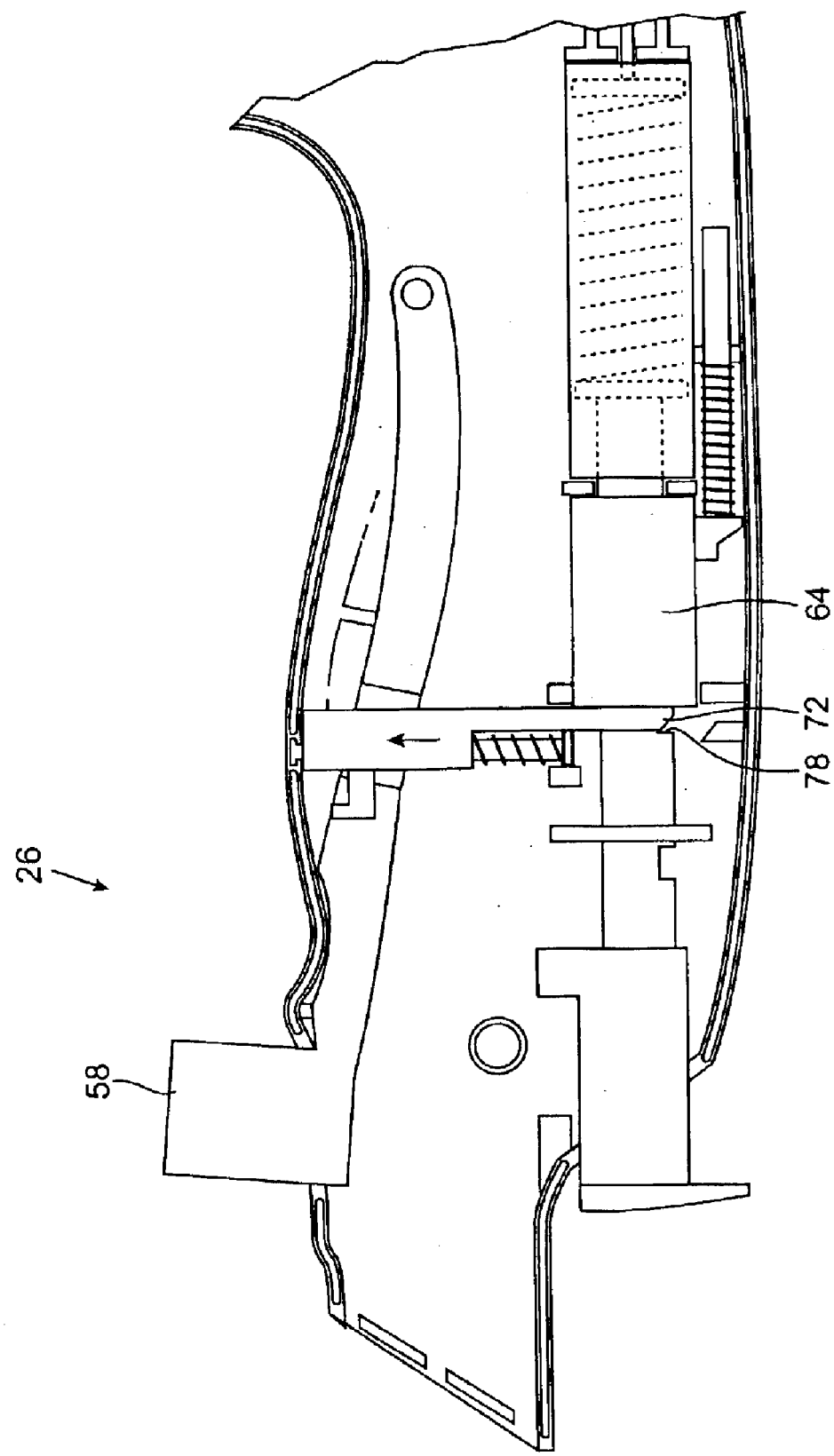
FIG. 6E is a close-up cut away elevational view of the proximal portion of the probe of FIG. 6A in which the plunger assembly is in an partially compressed configuration and the needle is in a partially retracted or treatment position.

In its maximum deployment position or "overtravel position," the needle is protruding through an aperture in the probe body. In one exemplary embodiment, a needle tip is deployed approximately 16 mm in a direction along the needle axis beyond the aperture. As shown in FIG. 6D, when lock guide 64 reaches its overtravel position, a lock 72 slides off lock guide 64 and can be forced upward (as illustrated by arrow 75) by a lock spring 74 to move. The movement of lock 72 causes a lock release lever 58 to move from its first, compressed position to a second, extended position (compare FIGS. 6C and 6D).

Advantageously, in exemplary configurations, a user will know if the needle is deployed based on the positions of plunger 56 and release button 58. At such point, an operator of the probe can be provided with tactile feedback as to the stopping of the travel of the plunger as the moving part will contact a reinforcing rib 76 within the probe body.

Additionally, the moving parts may create an audible sound, such as a "click" to inform the operator that needle 24 has reached its overtravel position. Such feedback (e.g., audible and tactile) lets the user know that the needle has traveled a requisite distance to allow the needle to be locked in its partially retracted position. If the needle and plunger do not reach the requisite point (e.g., full deployment), the plunger 56 will be biased back to its original position so as to move the needle back to the retracted position, and the needle will not lock in its partially retracted position. (FIG. 6B). It should be appreciated however, that while the preferred requisite distance is the maximum travel position, in other embodiment, the requisite distance can be a point less than the maximum travel position.

To move needle 24 to its partially retracted position (FIG. 6E), the operator can release the pressure on plunger 56 to allow a force from main spring coil 62 to bias the plunger to a partially retracted position. Lock guide 64 cannot move back to its original position because lock 72 has moved into its path. As the plunger continues to move toward its partially retracted, locked position, lock 72 engages a groove 78 in connector 68. This groove can lock the needle and the plunger in a treatment or partially retracted position. In one exemplary embodiment, the needle is protruding approximately 6.5 mm along the axis of the needle beyond the aperture in probe body 32. In the locked, partially retracted position, the plunger cannot be depressed since it is captured in position by lock 72 and the groove 78.

Figure 6F:
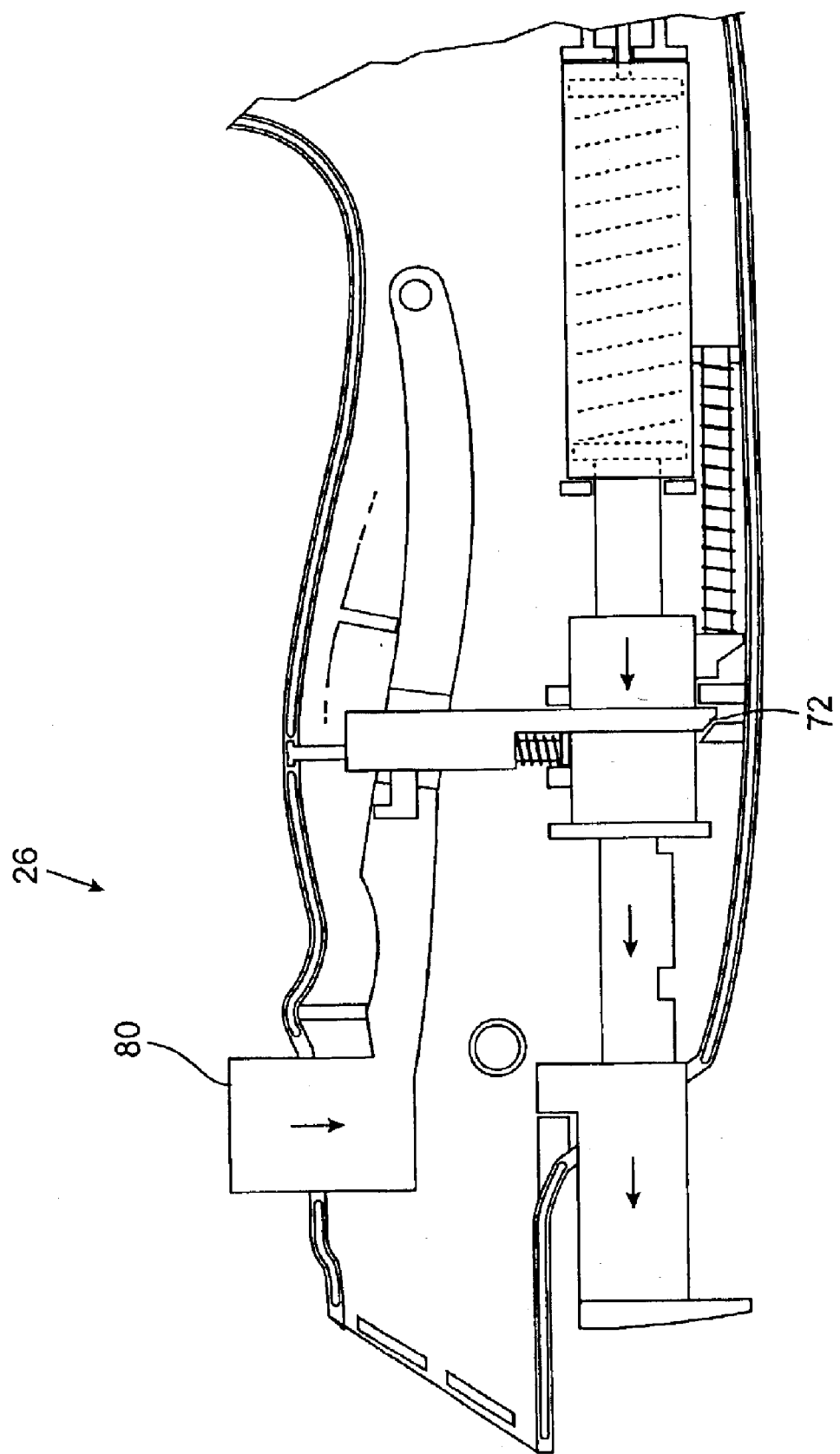
FIG. 6F is a close-up cut away elevational view of the proximal portion of the probe of FIG. 6A in which the release assembly is activated to return the needle and plunger assembly to its position in FIG. 6B.

As shown in FIG. 6F, when it is desired to return needle 24 to its retracted position within probe body 32, the user can depress release button 58 with an index finger (or other finger) in direction of arrow 80 so that lock 72 moves in a downward direction. Once lock 72 has reached an end of its travel, lock guide 64 under biasing pressure, slides through a hole in lock 72 and lock guide 64 and plunger 56 are biased by main coil spring 62 to its retracted position. (FIG. 6B).

Figure 7A:
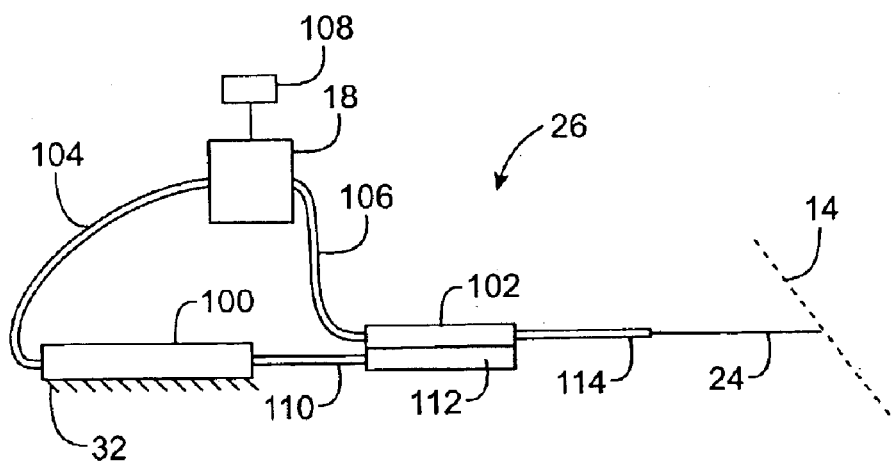
FIG. 7A schematically illustrates a pneumatic needle actuation device in which the needle is in a retracted position.

FIG. 7A schematically illustrates one exemplary probe 30 having a pneumatic needle actuation device 26. Actuation device 26 can include a series arrangement of pneumatic pistons or motors 100, 102 that use connectors 104, 106 to communicate with controller 18. Controller 18 can run a control routine to activate pneumatic motors 100, 102 to move needle 24 between the retracted position, fully extended position and partially extended position for temperature monitoring.

To deploy the needle, a user can activate an input device, such as a button 108 that is in communication with controller 18. Input device 108 can send a control signal to instruct controller 18 to deploy needle 24 to its deployed position in which needle tip 54 extends beyond the targeted treatment depth. In some embodiments, the controller can be programmed to automatically retract needle 24 to a partially retracted position. In such embodiments, the user will only have to activate a single input device to deploy and automatically retract the needle. In other embodiments, however, a user will be required to activate an input device (either input device 108 or another input device) to retract needle 24 to the partially retracted position. Similarly, to retract the needle to its completely retracted position, user can activate an input device (either input device 108 or a "retract" input device) to deliver a control signal to controller 18 to cause needle 24 to be returned to its original position.

In the illustrated embodiment, pneumatic motor 100 can be fixedly attached to probe body 32 such that upon activation of button 108, a control signal from controller 18 will be sent via connector 104 to pneumatic motor 100 such that a shaft 110 will extend its stroke distance from pneumatic motor 100. Pneumatic motor 102 can be coupled to shaft 110 of pneumatic motor with a coupling assembly 112, such that extension of shaft 110 moves the entire pneumatic motor 102.

Figure 7B:
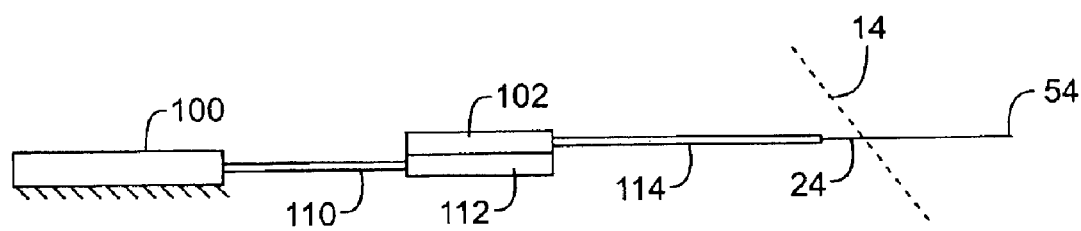
FIG. 7B schematically illustrates the pneumatic needle actuation device of FIG. 7A in which the needle is in a deployed position.

The activation of button 108 will also send a control signal to motor 102 through connector 106 to cause a shaft 114 of pneumatic motor 102 to extend its stroke distance. In such a position as shown in FIG. 7B, needle 24 that is carried by shaft 114 will be in its deployed position, beyond a tissue target zone.

To partially retract needle 24, so as to reduce a tenting of the tissue and to increase the tissue contact between the tissue contacting surfaces of probe 30 and the tissue surface, a second control signal can be sent (automatically or through actuation of an input device) to at least one of the pneumatic motors so as to retract needle 24.

In one configuration, controller 18 can be programmed to automatically retract needle 24 to its partially retracted position after a specified time period (e.g., approximately 500 ms) in which needle tip 54 is locked into a proper treatment depth immediately after reaching its deployed position. In such configurations, the user need only activate one input device to control the deployment and partial retraction of needle 24. In other configurations, however, the user may be required to activate input device 108 to partially retract needle 24. It should be appreciated however, that instead of activating input device 108, the user may activate a "retract" button that allows the user to control the retraction of the needle.

Figure 7C:
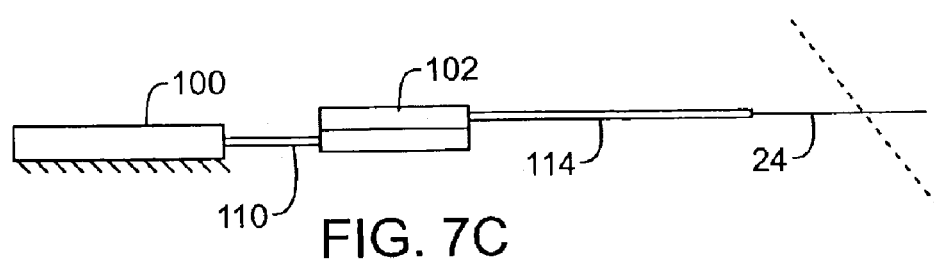
FIG. 7C schematically illustrates the pneumatic needle actuation device of FIG. 7A in a configuration in which the needle is in a partially retracted position.

In one exemplary embodiment illustrated in FIG. 7C, to retract needle 24 to a partially retracted position, a control signal can be sent to pneumatic motor 100 to retract shaft 110 to a retracted position (either the original position or another retracted position). In such embodiments, the position of shaft 114 will typically stay in its extended position.

Figure 7D:
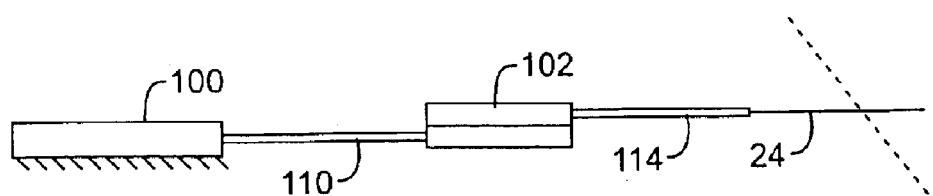
FIG. 7D schematically illustrates an alternative pneumatic needle actuation device of FIG. 7A in a configuration in which the needle is in a partially retracted position.

Alternatively, as shown in FIG. 7D, to retract needle 24 to a partially retracted position, a control signal can be sent to pneumatic motor 102 to retract shaft 114 to a retracted position (either the original position or another retracted position). In such embodiments, the position of shaft 110 will typically stay in its extended position.

In one tested configuration, pneumatic motor 100 has a stroke of approximately 6.37 mm (approximately 0.25 inches) and the second pneumatic cylinder 102 has a stroke of 12.7 mm (approximately 0.50 inches). Thus, in embodiments in which pneumatic motor 102 is retracted, the needle can be retracted more than approximately 10 mm from its full deployment length. It should be appreciated however, that the present invention is not limited to such pneumatic motors, and other pneumatic motors having different stroke lengths can be used so that the needle can be retracted between approximately 6 mm and 16 mm of the deployment distance.

Figures 7E, 7F:
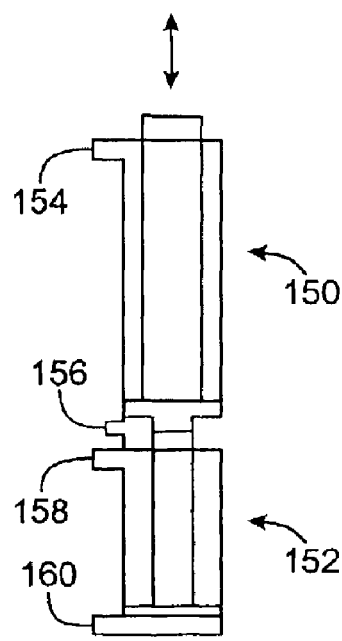
FIG. 7E illustrates one exemplary configuration of a pneumatic needle actuation device.
FIG. 7F is a chart illustrating a pressurization or exhaust of the ports of the pneumatic actuation device of FIG. 7E.

FIG. 7E illustrate one preferred configuration of a pneumatic needle actuation device 26. The illustrated assembly includes two pneumatic cylinders 150, 152. Each cylinder has two air ports 154, 156, 158, 160 for driving the piston of the cylinders to either end of its stroke by alternately pressurizing or exhausting the ports (e.g., opening to atmosphere).

FIG. 7F is a table illustrating the pressure/exhaust scheme for each desired position of the needle (e.g., retracted, deployed, and partially deployed), where "P" stands for pressurization of the port, and "E" stands for exhaust of the port. Thus, if the user desires the needle to be positioned in its retracted position, port 154 of cylinder 150 is pressurized and port 156 is exhausted. Port 158 of cylinder 152 is pressurized and port 160 is exhausted. To move the needle to its deployed position, ports 154 and 158 are exhausted while ports 156 and 160 are pressurized. To move the needle to a middle or partially retracted position, ports 154 and 160 are pressurized and ports 156 and 158 are exhausted. In other embodiments, however, to move the needle to its partially retracted position, it may be possible to have ports 156 and 158 pressurized and ports 154 and 160 exhausted.

Figure 7G:
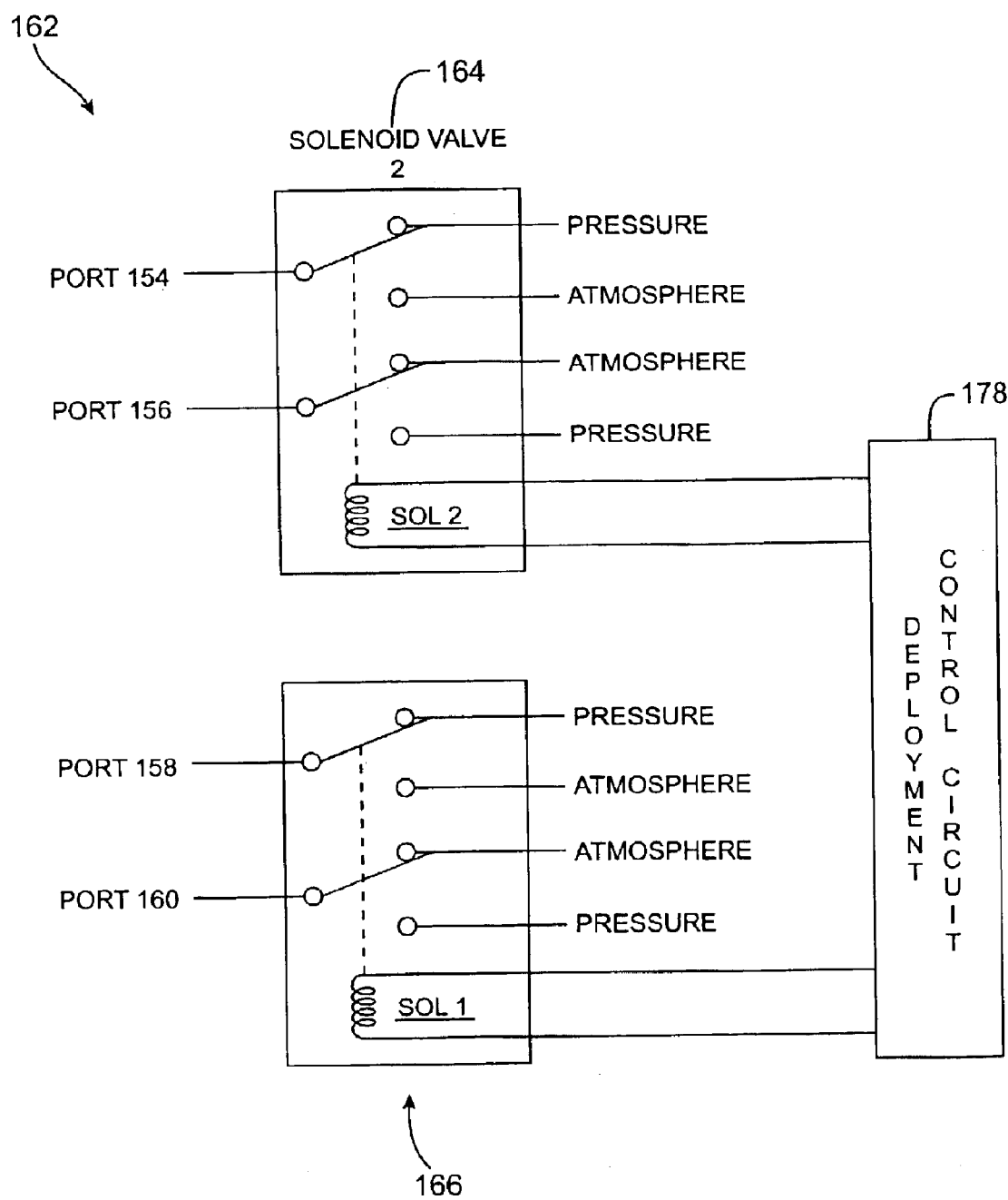
FIG. 7G schematically illustrates a control of a dual piston pneumatic actuation device.

FIG. 7G schematically illustrates one exemplary control 162 of the dual pneumatic piston assembly illustrated in FIG. 7E. Each cylinder's air ports can be connected to a two pole, two position valve 164, 166. Each of the valve's position can be controlled electrically by a solenoid Sol1, Sol2. The valve can be plumbed such that when one port is pressurized, the other port is open to the atmosphere (e.g., exhaust). Activating the solenoid reverses which port is pressurized and which is open to exhaust.

Figure 7H:
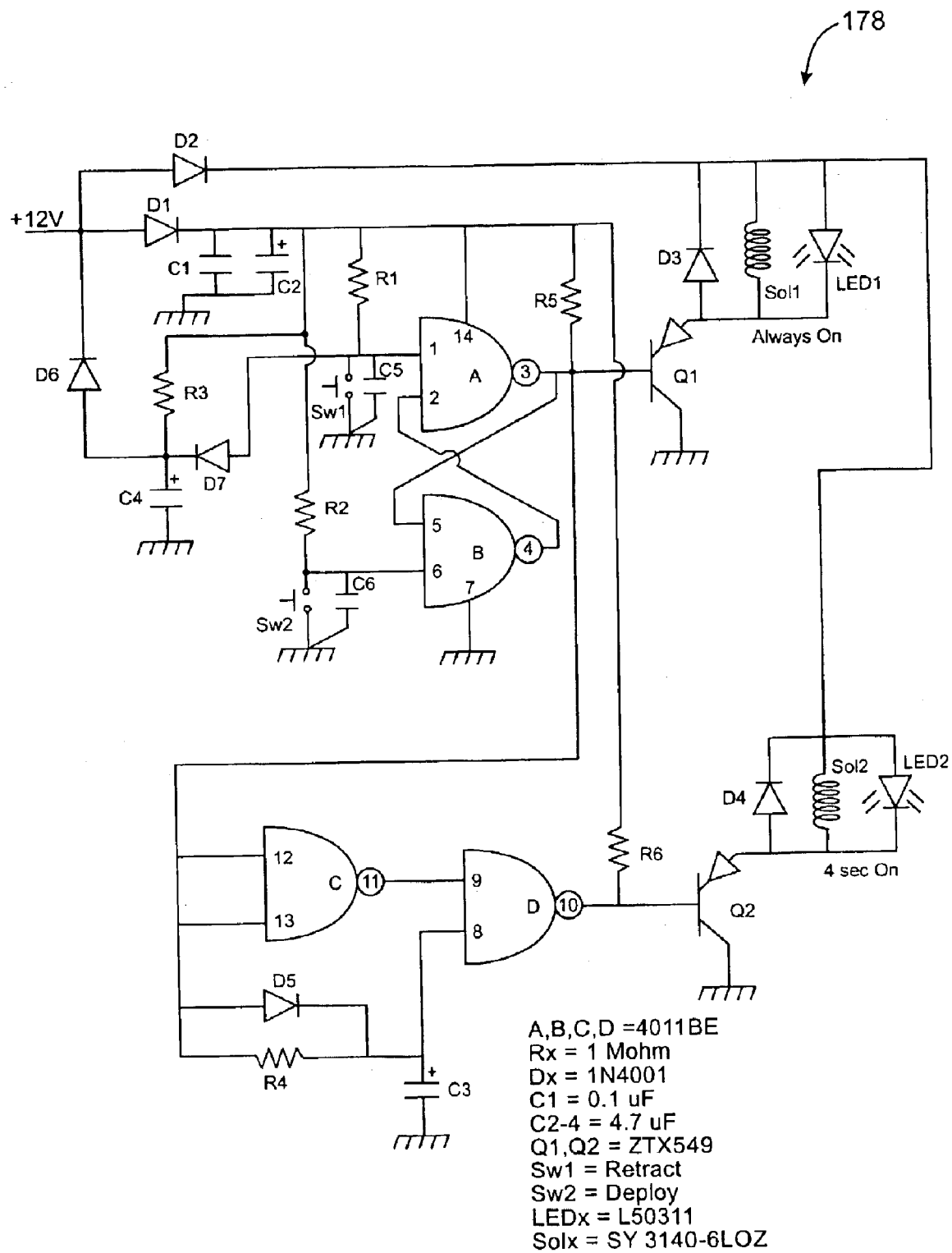
FIG. 7H schematically illustrates one exemplary deployment control circuit.

The sequencing of the solenoid valves can be controlled by an electronic deployment circuit 178 illustrated in FIG. 7H. The deployment circuit can energize and de-energize the solenoid valves (Sol1 and Sol2) in response to switch inputs Sw1, Sw2 from the user or controller. Initially both switches can be open and both solenoids are de-energized, so that the pistons are in the fully retracted position. Closing Sw2 causes a memory circuit to change state and to immediately activate both solenoids Sol1, Sol2 so that both pistons cylinders 150, 152 are in the fully deployed position.

The memory circuit allows Sw2 to be released at any time without altering the deployment position. When the memory circuit changes state, it also starts the discharge of a timing delay circuit comprised of R4, C3, and D5. The values of R4 and C3 can be selected such that after a selected time period, typically between one to four seconds, the voltage across C3 has declined to an appropriate level so as to disable Sol2. In this embodiment, Sol1 remains active, so that the pistons (and needle) are moved to a partially extended position for temperature monitoring of the target zone tissue.

Deployment circuit 172 can maintain this condition until Sw1 is closed. Closing of Sw1 can reset the memory circuit, causing Sol1 to de-energize immediately. Closing Sw1 can also de-energize Sol2 (assuming that it is energized at the time). Diode D5 can rapidly recharge C3 when the memory circuit resets to prepare for the next deployment cycle.

It should be appreciated however, that in other alternative embodiments, Sol1 can be disabled and Sol2 can remain active to move the pistons and needle to its partially retracted position.

It should be appreciated, that in some embodiments, as one optional safety measure, the controller can be configured to allow the user to retract the needle at any time during the procedure. The circuit illustrated in FIG. 7H accomplishes this by giving priority to the state of Sw1 over Sw2. Closing Sw1 can reset the memory circuit to the solenoid de-energized position, regardless of the position of Sw2. If both switches Sw1, Sw2 are closed, the solenoids can remain de-energized.

An additional optional safety consideration is that deployment circuit 172 may be configured to always initialize to the fully retracted position upon application of electrical power. This can be provided for by timing the delay circuit that is comprised of R1, R3, C4, and D7. Upon application of electrical power, the memory circuit (gates A and B) can be maintained in the reset condition for several seconds (e.g., two to four seconds), until the voltage across C4 has risen to an appropriate level to enable the memory circuit.

Yet another optional safety consideration is that the needle can not be inadvertently extended due to an interruption of circuit power that will cause a malfunction in deployment circuit 172. This safety consideration can be incorporated by providing a timing delay circuit comprised of D6, D7, and C4 and the energy storage circuit of D1 and C2. Upon interruption of circuit power, diode D6 will cause the voltage across C4 to decline rapidly so as to cause the memory circuit to immediately reset to the solenoid off condition (e.g., needle in the retracted position). Meanwhile, diode D1 can disconnect the memory circuit from the source of the interrupted power and capacitor C2 can provide several seconds of power (e.g., two to four seconds) to the memory circuit to ensure that the memory circuit continues to operate properly until the solenoids Sol1, Sol2 can no longer energize due to the interruption of power.

It should be appreciated however, that other conventional or proprietary needle actuation devices can be used to deploy and partially retract the needle. For example, the needle actuation device can include a linear motor actuator having a two pole moving magnet DC linear motor that is configured to move the needle from a retracted position, to a deployed position, and to a partially retracted position.

Figure 8:
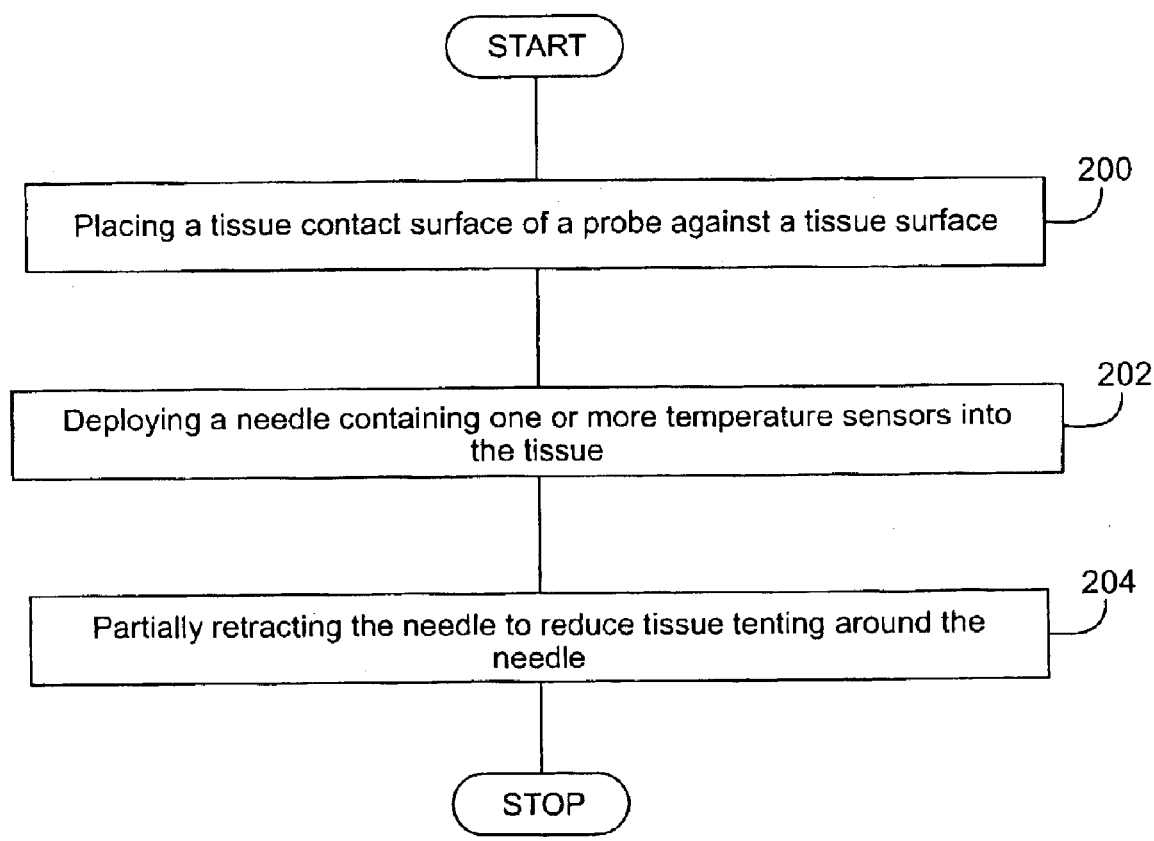
FIG. 8 schematically illustrates an exemplary method of the present invention.

Some exemplary methods of the present invention will now be described. As shown schematically in FIG. 8, a tissue contact surface of a probe can be placed against a tissue surface (Step 200). To sense the temperature of the target zone, a needle containing one or more temperature sensors can be deployed into the tissue. The needle can be partially retracted to reduce (and preferably eliminate) tissue tenting around the needle. (Steps 202, 204). Elimination of the tissue tenting increases the amount of tissue contacting the tissue contact surface (e.g., cooled electrode surface) and reduces the amount of collateral damage to the tissue surface from the delivery of energy from the electrodes.

Figure 9:
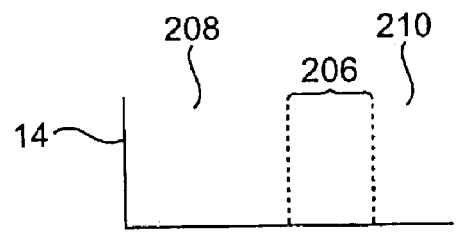
FIGS. 9 to 9E graphically illustrate a temperature cycle for a target tissue and an intermediate tissue.
Figure 9A:
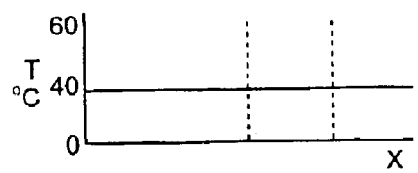
Figure 9B:
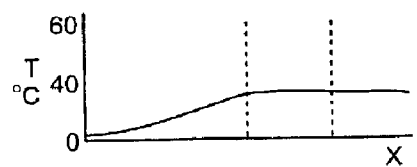
Figure 9C:
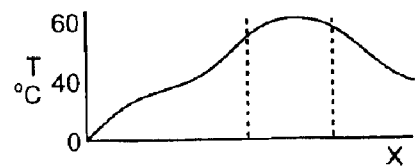
Figure 9D:
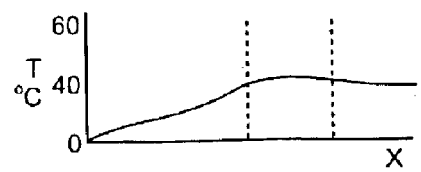
Figure 9E:
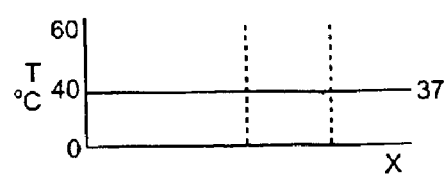

As can be understood with reference to FIGS. 9–9E, the tissue can be cooled before (e.g. pre-cooling) and after energizing (e.g., post-cooling) of the electrodes. FIG. 9 illustrates three distinct regions of tissue T disposed adjacent electrode 12—a target zone 206, an intermediate tissue 208, and a tissue 210 beyond the target zone. Target zone 206 will typically comprise fascia or some other collagenated tissue, while surfaces of the electrodes 14 contact an intermediate tissue 208 disposed adjacent the fascia.

It will generally be desirable to maintain the temperature of intermediate tissue 208 below a maximum safe tissue temperature to prevent injury to this intermediate tissue, the maximum safe tissue temperature typically being about 45° C. To effect shrinkage of fascia, target zone 206 will typically be heated to a temperature above about 60° C., and often to a temperature at or above 70° C.

As illustrated in FIG. 9A, prior to application of cooling or heating energy, the temperature profile of tissue T along an axis X adjacent electrode 12 is substantially uniform at body temperature (approximately 37° C.). The tissue will preferably be pre-cooled by the surfaces of electrodes 14, generally using an electrode surface temperature of at or above 0° C. Pre-cooling will substantially decrease the temperature of intermediate tissues 208. At least a portion of the target zone remains at or near the initial body temperature, as illustrated in FIG. 9B. Pre-cooling time will often depend on electrode separation and tissue heat diffusivity.

Referring now to FIG. 9B, intermediate tissue 208 exhibits a substantial temperature differential as compared to target tissue 206. As a result of this temperature differential, the electrical impedance of an immediate tissue 208 has been enhanced relative to target tissue 206. This does not necessarily mean that the impedance of the intermediate tissue is now greater than that of the target tissue (although this will often be the case). Regardless, as compared to the tissues at uniform body temperature, the temperature differential between the target and intermediate tissues can now be used to help enhance selective heating of the target tissue while minimizing collateral damage to the adjacent tissue.

Once the tissue has been pre-cooled, the RF current is directed through the tissue between the electrodes to heat the tissue. In exemplary methods, a temperature sensor 22 can be deployed beyond target zone 206 and retracted to a point near a center of target zone 206 to help determine when the pre-cooling has been applied for the proper time to initiate RF heating. The current flux applies a fairly uniform heating throughout the tissue between the electrodes 12, and electrode surfaces 14 are often cooled throughout the heating process. As noted above, partial retraction of needle 24 improves contact between the tissue surface and the electrodes so as to reduce or eliminate tissue tenting around needle 24.

As target zone 206 has the higher temperature relative to the intermediate tissue 208 upon initiation of the heating cycle, and as the target zone is farther from cooled electrodes 12, a relatively small amount of heat flows from the target zone into cooled electrodes 12, and the target zone is heated to a significantly higher temperature than intermediate tissue 208.

Heat is applied until the target zone is at or above a treatment temperature, typically resulting in a temperature distribution such as that illustrated in FIG. 9C. To minimize collateral damage to the adjacent tissues 208, the cooling assembly 16 continues to circulate cold fluid through the electrode 12, and to remove heat from the tissue, after the heating radiofrequency energy is halted. When substantially the entire tissue is below the maximum safe tissue temperature (as in FIG. 9D), cooling can be halted, and the tissue can be allowed to return to standard body temperature, as illustrated in FIG. 9E.

It should be appreciated that there are a variety of electrode assemblies that can be used to deliver a heating energy to the target tissue. For example, instead of delivering RF current from the electrode assembly of FIG. 2, it may be possible to deliver RF current driven between two cooled plate electrodes using intermittent pulses of excitation. As used herein, intermittent or pulsed excitation encompasses cyclically increasing and decreasing delivered power, including cyclical variations in RMS power provided by amplitude modulation, waveform shape modulation, pulse width modulation, or the like. Such intermittent excitation will preferably provide no more than about 25% of the RMS power of the pulses during the intervals between pulses. Preferably, the electrodes will be energized for between about 10 and 50% of a total heating session. For example, electrodes 12 may be energized for 15 seconds and then turned off for 15 seconds and then cycled on and off again repeatedly until the target tissue has been heated sufficiently to effect the desired shrinkage. Preferably, electrode surfaces 14 (and the surrounding probe structure which engages the tissue) will be cooled throughout the on/off cycles of the heating sessions.

In alternative embodiments, pre-chilling time, the duration of the heat, the lengths of the heating intervals (and the time between heating intervals) during intermittent heating, and the radiofrequency heating current may be controlled without having direct feedback by using dosimetry. Where the thermal properties of these tissues are sufficiently predictable, the effect of treatment can be estimated from previous measurements.

FIGS. 10A to 10F illustrate some experimental results using some exemplary needle actuation devices of the present invention that deploy and retract needle 24. In obtaining the data, the variables were (1) the pressure applied to the tissue with the probe body, (2) the force/pressure of the needle deployment, and (3) the type of actuation mechanism (e.g., pneumatic, linear motor, or manual deployment).

As shown by FIGS. 10A to 10F, for each of the different actuation mechanisms, each of the elliptical shaped tissue tenting regions undergo a change in area over time. Upon insertion of needle 24 into the tissue, a maximum tenting region 220 occurs. After a time period, the tissue relaxes and the tenting region relaxes to a tenting plateau 222. After needle 24 is partially retracted, the tenting region is reduced, and preferably eliminated. Without partial retraction of the needle, the tissue tenting region would be maintained at tenting plateau 222 and out of contact with a tissue contacting surface of a probe body.

The data obtained from the experiments suggests that the size of the maximum tenting region and plateau tenting region is dependent on the pressure that the probe body exerts on the tissue. As shown by FIGS. 10A to 10F, lines 224 refer to an applied pressure of 4.60 psi while lines 226 refer to an applied pressure of 1.94 psi. As seen in the Figures, the higher applied pressure from the probe body significantly reduces the tenting region surface area of the maximum tenting region 220 and plateau tenting region 222.

Figure 10A:
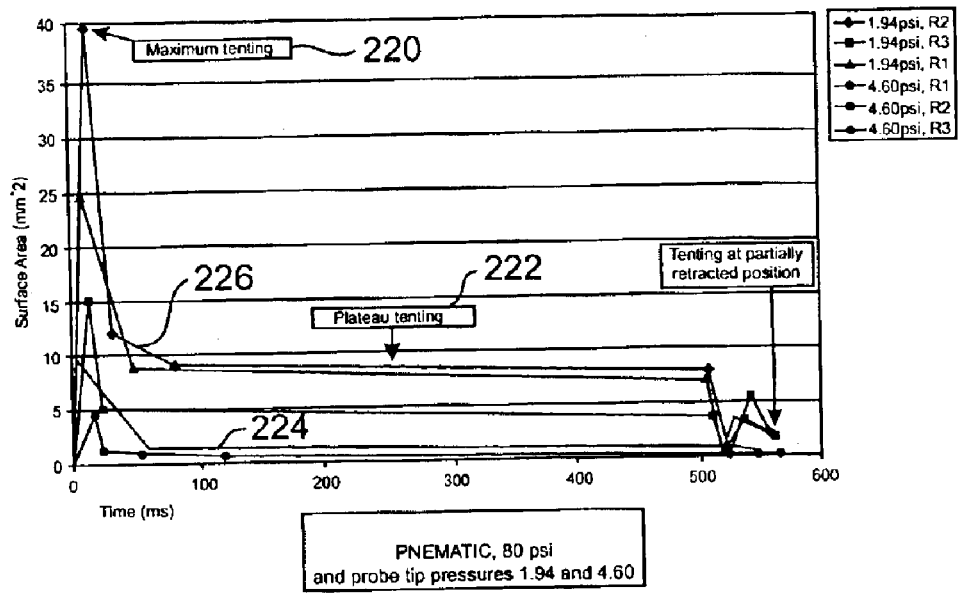
FIGS. 10A to 10F illustrate some experimental results of the present invention in which the force of the needle, pressure applied to the tissue, and needle actuation devices were varied.
Figure 10B:
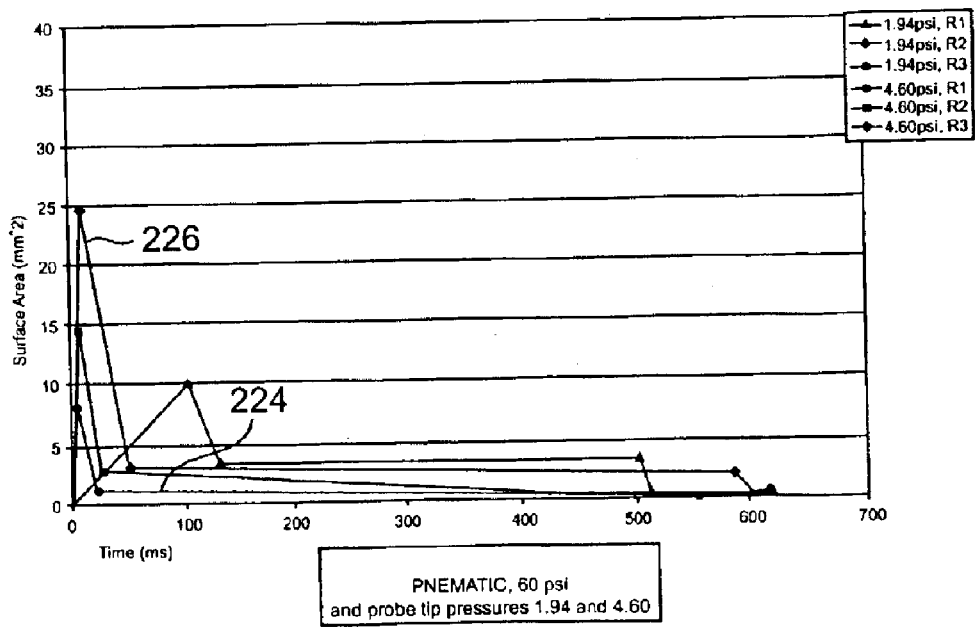
Figure 10C:
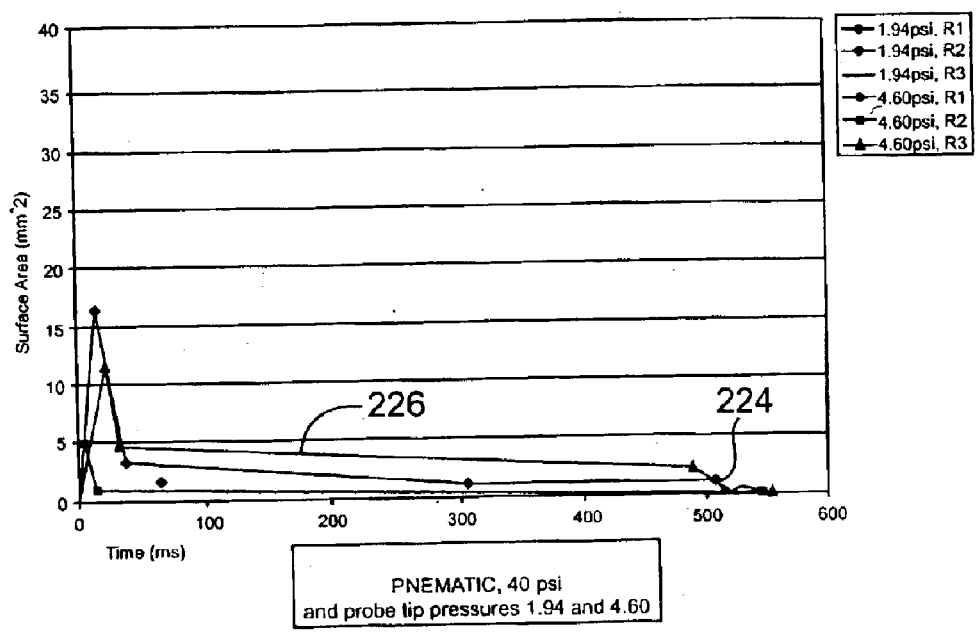
Figure 10D:
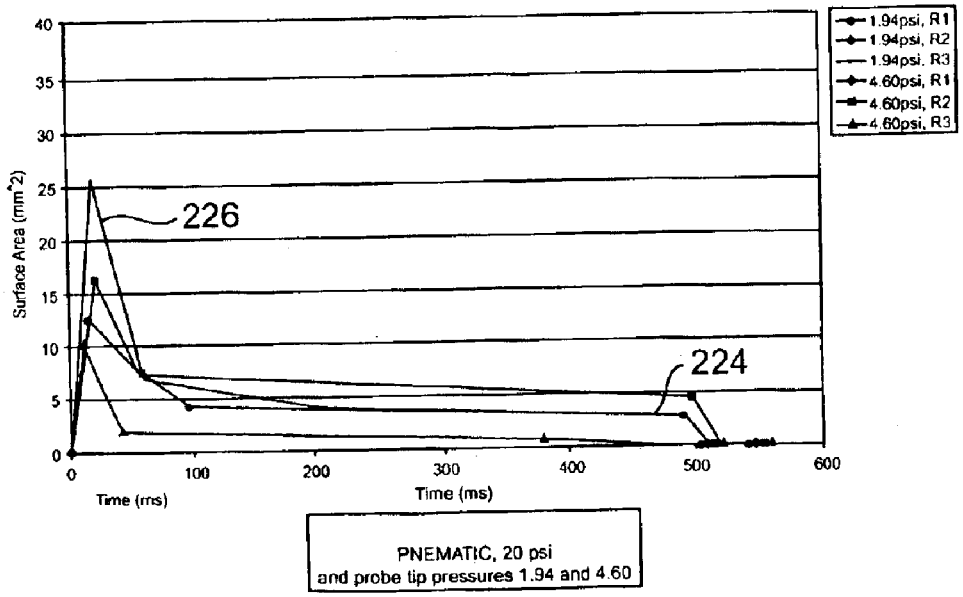
Figure 10E:
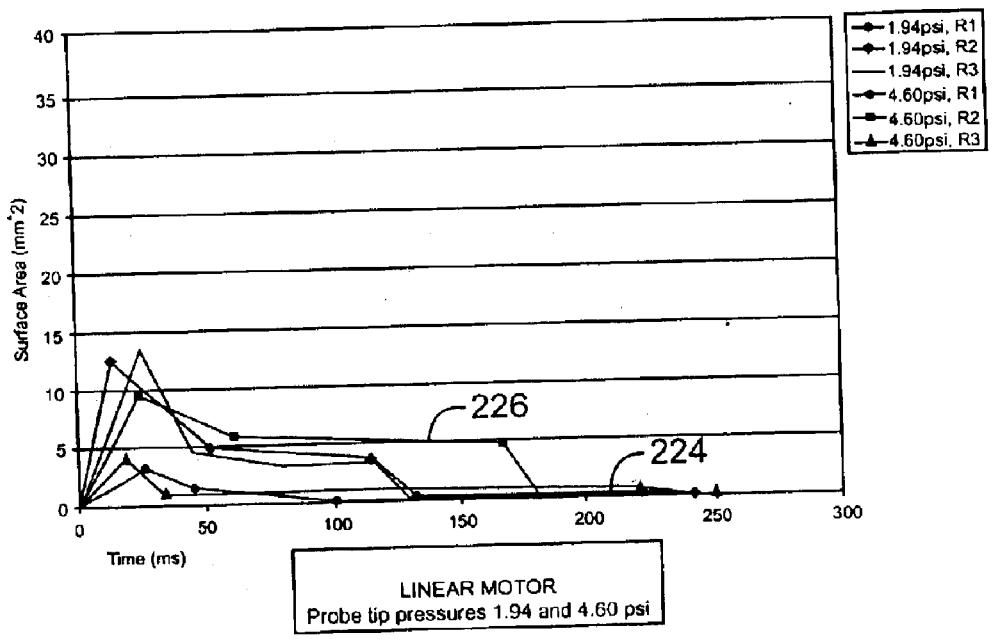
Figure 10F:
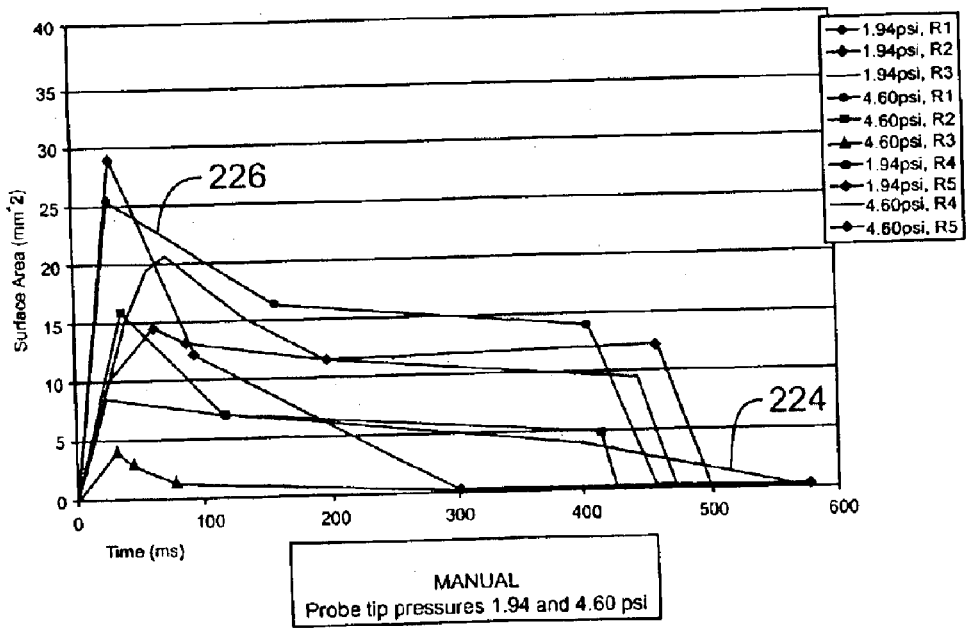

For example, referring to FIG. 10A in which the needle was deployed at 80 psi and a probe pressure of 1.94 psi, the average maximum tenting region was approximately 27.9 mm$^2$, while after partial retraction of the needle, the area of the remaining tenting is approximately 1.09 mm$^2$. For the probe pressure of 4.60 psi, the maximum tenting region was approximately 8.61 mm$^2$ while the remaining tenting region after partial retraction was only 0.21 mm$^2$.

Referring now to FIGS. 10A to 10D, in which the pressure of the needle deployment was varied from 80 psi (FIG. 10A) to 20 psi (FIG. 10D), the data suggests that the pressure of the needle deployment is not linearly related to the size of the tenting region, but the pressure/force of the needle deployment does affect the size of the tenting region.

From the experiments it was determined that a force, typically between approximately 0.94 lbf and 6.14 lbf, and preferably between about 1.15 lbf and 1.45 lbf, was needed to deploy the needle into the tissue. It should be appreciated however, that the minimum force needed to deploy the needle may differ between the type of needle actuation device employed, the tension in the tissue, the tissue type and the like. For example, it was found that for the pneumatic motor assembly a minimum force to deploy the needle was approximately 1.15 lbf, while for the manual actuation device, the minimum force needed to deploy needle 24 into the tissue was approximately 1.43 lbf and for the linear motor, a minimum force of approximately 1.76 lbf was needed to deploy the needle into the tissue. It should be appreciated however, that the above force measurements are merely examples, and that the present invention should not be limited to such pressures and forces. For example, the tissue characteristics, needle size, and needle actuation devices may affect the force parameters required to deploy and retract the needle.

While the exemplary embodiments have been described in some detail, by way of example and for clarity of understanding, a variety of modifications, adaptations, and changes will be obvious to those who skill in the art. For example, needle sizes, needle types, tissue characteristics (such as density, composition, and elasticity) are variables that may affect the needle actuation device to deploy and retract the needle to reduce tenting. Additionally, instead of deploying the needle tip beyond the target zone, the needle can be deployed into the target zone and retracted to a point still within the target zone. Further, it may be possible to deploy the needle tip beyond the target zone and retract the needle to a point where the needle tip is still beyond the target zone.

Additionally, instead of retracting the needle, it may be possible to manufacture a needle having a reduced friction coefficient so that tenting is reduced to a negligible amount. Moreover, it may be possible to create an aspiration or suction on the probe tip to reduce the tenting. Therefore, the scope of the present invention is limited solely by the appended claims.

What is claimed is:

1. A method for improving contact with a surface of a tissue, the method comprising:
   placing a tissue contacting surface of a probe body against the surface of the tissue, wherein the tissue contacting surface of the probe body comprises a surface of at least one electrode;
   deploying a needle into the tissue;
   partially retracting the needle to increase the amount of contact between the tissue contacting surface of the probe body and the surface of the tissue.

2. The method of claim 1 wherein the at least one electrode is cooled.

3. The method of claim 1 wherein placing comprises applying a pressure against the surface of the tissue.

4. The method of claim 1 wherein the needle is deployed into the tissue between approximately 10 mm and 20 mm, and the needle is partially retracted between 6 mm and 11 mm.

5. The method of claim 1 wherein the tissue is selected from the group consisting of a urethral wall, a bladder, a bladder neck, a ureter, bladder suspension ligaments, a sphincter, a pelvic ligament, a pelvic floor muscle, and fascia.

6. The method of claim 1 comprising measuring a temperature of the tissue with the needle;
   delivering a heating energy into the tissue; and
   adjusting a power level of the heating energy in response to the measured temperature.

7. The method of claim 6 wherein delivering is applied as a bipolar RF energy transmitted between a plurality of electrodes.

8. The method of claim 1 wherein deploying the needle comprises positioning a tip of the needle beyond a target tissue.

9. The method of claim 1 wherein partially retracting the needle comprises positioning a tip of the needle adjacent a target tissue.

10. The method of claim 1 wherein deploying comprises advancing the needle at an angle from the tissue contacting surface.

11. The method of claim 1 wherein deploying is carried out with a pneumatic motor.

12. The method of claim 1 wherein deploying is carried out with a linear motor.

13. The method of claim 1 wherein deploying is carried out with a mechanical plunger.

14. The method of claim 1 wherein the increase the amount of contact comprises reducing a tenting in the surface of the tissue around the needle.

15. A method of improving tissue contact between tissue and a probe, the method comprising;
   contacting a tissue contacting surface of the probe against the tissue, wherein the tissue contacting surface of the probe body comprises a surface of at least one electrode;
   deploying a needle into the patient tissue; and
   a step for reducing tissue tenting around the needle so that tissue substantially maintains contact with the tissue contacting surface of the probe.

16. The method of claim 15 comprising delivering electrical energy into the tissue.

17. The method of claim 15 wherein the needle is deployed into the tissue between approximately 10 mm and 20 mm, wherein the step for reducing tissue tenting comprises retracting the needle between approximately 6 mm and 11 mm.

18. The method of claim 15, wherein the at least one electrode comprises a plurality of electrodes, the method comprising delivering a heating energy to the tissue through a plurality of electrodes.

19. The method of claim 18 wherein delivering comprises effecting shrinking of collagenous structures within the tissue to inhibit urinary incontinence.

20. The method of claim 19 wherein the collagenous tissue structure is selected from the group consisting of a urethral wall, a bladder, a bladder neck, a ureter, bladder suspension ligaments, a sphincter, a pelvic ligament, a pelvic floor muscle, and fascia.

21. The method of claim 18 comprising measuring a temperature of the tissue with the needle,
wherein delivering comprises adjusting a power level of the heating energy, wherein adjusting is performed in response to the measured temperature.

22. The method of claim 18 wherein delivering is applied as a bipolar RF energy transmitted between the plurality of electrodes.

23. The method of claim 15 wherein deploying the needle comprises positioning a tip of the needle beyond a target tissue.

24. The method of claim 15 wherein deploying comprises advancing the needle at an angle from the tissue contacting surface.

25. The method of claim 15 wherein deploying is carried out with a pneumatic motor.

26. The method of claim 15 wherein deploying is carried out with a linear motor.

27. The method of claim 15 wherein deploying is carried out with a mechanical plunger.

28. The method of claim 27 wherein the step for reducing tissue tenting is carried out only if the mechanical plunger is moved to a fully deployed position.

29. The method of claim 15 wherein the needle is deployed through an aperture in the probe.

30. A device for treating a target tissue, the target tissue having a tissue surface, the device comprising:
a body comprising a tissue contacting surface that contacts the tissue surface, wherein the tissue contacting surface of the body comprises a surface of at least one electrode;
a needle movably coupled to the body, the needle comprising a tip that is movable from a retracted position to a deployed position,
wherein the needle tip can be moved from the deployed position and locked into a partially retracted position.

31. The device of claim 30 wherein the needle tip in the deployed position is positioned beyond the target tissue.

32. The device of claim 30 wherein the needle tip in the partially retracted position is located within the target tissue and increases the amount of surface contact between the tissue surface and the tissue contacting surface.

33. The device of claim 30 comprising a needle deployment mechanism coupled to the needle.

34. The device of claim 33 wherein the needle deployment mechanism comprises a pneumatic motor.

35. The device of claim 33 wherein the needle deployment mechanism comprises a linear motor.

36. The device of claim 33 wherein the needle deployment mechanism comprises a mechanical plunger.

37. The device of claim 30 wherein the body defines a tangential plane, wherein the needle is deployed at a non-orthogonal angle from the plane.

38. The device of claim 30 wherein the body defines a tangential plane, wherein the needle is deployed at an orthogonal angle from the plane.

39. The device of claim 30 wherein the needle tip comprises a temperature sensor.

40. The device of claim 30 wherein the needle tip comprises an electrode.

41. The device of claim 30 wherein the needle is advanceable through an aperture in the body.

42. The device of claim 30 wherein the needle in the partially retracted position reduces a tissue tenting in the tissue surface.

43. A system for treating a target tissue of a patient body, the target tissue having a tissue surface, the system comprising:
a probe body comprising a proximal portion and a distal portion, said distal portion comprising a tissue contacting surface;
a plurality of electrodes positioned on the distal portion of the probe body, wherein the tissue contacting surface of the distal portion comprises a surface of at least one electrode;
a power source coupled to the plurality of electrodes;
a needle comprising a tip;
actuation means for moving the needle between a first position, a second position, and a third position, wherein the needle in the first position is housed within the distal portion of the probe body, wherein the needle in the second position is extended such that the needle tip is beyond the target tissue, and the needle in the third position is retracted from the second position such that the needle tip is positioned in the target tissue.

44. The system of claim 43 wherein the needle in the third position increases an amount of contact between the tissue surface and the plurality of electrodes.

45. The system of claim 43 comprising a cooling assembly that cools the plurality of electrodes.

46. The system of claim 43 wherein the proximal portion comprises a user actuatable device to move the needle between the first position, second position, and third position.

47. The system of claim 43 wherein the user actuatable device comprises a plunger and a release button.

48. The system of claim 43 wherein the user actuatable device comprises at least one button coupled to a processor that is in communication with the actuation means.

49. The method of claim 1 wherein deploying comprises positioning a needle tip beyond a target zone, wherein partially retracting comprises positioning the needle tip beyond the target zone.

50. The method of claim 1 comprising positioning a first sensor at a tip of the needle and a second sensor along a shaft of the needle.

51. The method of claim 50 wherein in the partially retracted position, the first sensor is positioned beyond a target tissue and the second sensor is in the target tissue.

52. The method of claim 50 wherein in the partially retracted position, the first sensor is in the target tissue and the second sensor is positioned in an intermediate tissue.

53. The method of claim 50 further comprising positioning a third sensor along the shaft of the needle, wherein in the partially retracted position the first sensor is positioned beyond a target tissue, the second sensor is in the target tissue, and the third sensor is positioned in an intermediate tissue.

54. The method of claim 50 further comprising positioning a third sensor along the shaft of the needle, wherein in the partially retracted position the first sensor is positioned in a target tissue, and the second sensor and third sensor are positioned in an intermediate tissue.

55. The method of claim 50 wherein the first sensor and second sensor are temperature sensors.

56. The method of claim 11 wherein a single user actuation device is coupled to the pneumatic motor for automatically deploying and partially retracting the needle.

57. The method of claim 13 wherein the needle is partially retracted only if the mechanical plunger is moved to a fully compressed position.

58. A method of operating a probe, the method comprising:
- placing a tissue contacting surface of a probe body against the surface of the tissue, wherein the tissue contacting surface of the probe body comprises a surface of at least one electrode;
- deploying a needle into the tissue to a deployed position;
- partially retracting the needle from the deployed position; and
- locking the needle in a partially retracted position.

59. The method of claim 1, wherein the probe body comprises the needle.

60. The method of claim 1, wherein the needle is not affixed to or advanceable from the probe body.

61. The method of claim 15, wherein the probe comprises the needle.

62. The method of claim 15, wherein the needle is not affixed to or advanceable from the probe.

* * * * *